(12) United States Patent
Taylor

(10) Patent No.: US 7,636,703 B2
(45) Date of Patent: Dec. 22, 2009

(54) METHOD AND APPARATUS FOR APPROXIMATE PATTERN MATCHING

(75) Inventor: David Edward Taylor, St. Louis, MO (US)

(73) Assignee: Exegy Incorporated, St. Louis, MO (US)

( * ) Notice: Subject to any disclaimer, the term of this patent is extended or adjusted under 35 U.S.C. 154(b) by 223 days.

(21) Appl. No.: 11/381,214

(22) Filed: May 2, 2006

(65) Prior Publication Data

US 2007/0260602 A1    Nov. 8, 2007

(51) Int. Cl.
*G06F 15/00*    (2006.01)
(52) U.S. Cl. ....................................................... 706/62
(58) Field of Classification Search .................. None
See application file for complete search history.

(56) References Cited

U.S. PATENT DOCUMENTS

| | | | |
|---|---|---|---|
| 3,601,808 A | 8/1971 | Vlack | |
| 3,611,314 A | 10/1971 | Pritchard et al. | |
| 3,729,712 A | 4/1973 | Glassman | |
| 3,824,375 A | 7/1974 | Gross et al. | |
| 3,848,235 A | 11/1974 | Lewis et al. | |
| 3,906,455 A | 9/1975 | Houston et al. | |
| 4,081,607 A | 3/1978 | Vitols et al. | |
| 4,298,898 A | 11/1981 | Cardot | |
| 4,314,356 A | 2/1982 | Scarbrough | |
| 4,385,393 A | 5/1983 | Chaure et al. | |
| 4,464,718 A | 8/1984 | Dixon et al. | |
| 4,550,436 A | 10/1985 | Freeman et al. | |
| 4,823,306 A | 4/1989 | Barbic et al. | |
| 4,941,178 A | 7/1990 | Chuang | |
| 5,023,910 A | 6/1991 | Thomson | |
| 5,050,075 A | 9/1991 | Herman et al. | |
| 5,101,424 A | 3/1992 | Clayton et al. | |
| 5,140,692 A | 8/1992 | Morita | |
| 5,163,131 A | 11/1992 | Row et al. | |

(Continued)

FOREIGN PATENT DOCUMENTS

EP    0880088    11/1996

(Continued)

OTHER PUBLICATIONS

'Models, algorithms, and architectures for scalable packet classification': Taylor, Turner, Washington University.*

(Continued)

*Primary Examiner*—David R Vincent
*Assistant Examiner*—Peter Coughlan
(74) *Attorney, Agent, or Firm*—Thompson Coburn LLP

(57) ABSTRACT

A system and method for inspecting a data stream for data segments matching one or more patterns each having a predetermined allowable error, which includes filtering a data stream for a plurality of patterns of symbol combinations with a plurality of parallel filter mechanisms, detecting a plurality of potential pattern piece matches, identifying a plurality of potentially matching patterns, reducing the identified plurality of potentially matching patterns to a set of potentially matching patterns with a reduction stage, providing associated data and the reduced set of potentially matching patterns, each having an associated allowable error, to a verification stage, and verifying presence of a pattern match in the data stream from the plurality of patterns of symbol combinations and associated allowable errors with the verification stage.

95 Claims, 6 Drawing Sheets

U.S. PATENT DOCUMENTS

| | | |
|---|---|---|
| 5,179,626 A | 1/1993 | Thomson |
| 5,226,165 A | 7/1993 | Martin |
| 5,243,655 A | 9/1993 | Wang |
| 5,249,292 A | 9/1993 | Chiappa |
| 5,255,136 A | 10/1993 | Machado et al. |
| 5,265,065 A | 11/1993 | Turtle |
| 5,319,776 A | 6/1994 | Hile et al. |
| 5,327,521 A | 7/1994 | Savic et al. |
| 5,339,411 A | 8/1994 | Heaton, Jr. |
| 5,371,794 A | 12/1994 | Diffie et al. |
| 5,388,259 A | 2/1995 | Fleischman et al. |
| 5,396,253 A | 3/1995 | Chia |
| 5,418,951 A | 5/1995 | Damashek |
| 5,432,822 A | 7/1995 | Kaewell, Jr. |
| 5,440,723 A | 8/1995 | Arnold et al. |
| 5,461,712 A | 10/1995 | Chelstowski et al. |
| 5,465,353 A | 11/1995 | Hull et al. |
| 5,481,735 A | 1/1996 | Mortensen et al. |
| 5,488,725 A | 1/1996 | Turtle et al. |
| 5,497,488 A | 3/1996 | Akizawa et al. |
| 5,544,352 A | 8/1996 | Egger |
| 5,546,578 A | 8/1996 | Takada |
| 5,651,125 A | 7/1997 | Witt et al. |
| 5,701,464 A | 12/1997 | Aucsmith |
| 5,721,898 A | 2/1998 | Beardsley et al. |
| 5,740,244 A | 4/1998 | Indeck et al. |
| 5,740,466 A | 4/1998 | Geldman |
| 5,774,835 A | 6/1998 | Ozawa |
| 5,774,839 A | 6/1998 | Shlomot |
| 5,781,772 A | 7/1998 | Wilkinson, III et al. |
| 5,781,921 A | 7/1998 | Nichols |
| 5,805,832 A | 9/1998 | Brown et al. |
| 5,813,000 A | 9/1998 | Furlani |
| 5,819,273 A | 10/1998 | Vora et al. |
| 5,819,290 A | 10/1998 | Fujita |
| 5,826,075 A | 10/1998 | Bealkowski et al. |
| 5,864,738 A | 1/1999 | Kessler et al. |
| 5,913,211 A | 6/1999 | Nitta |
| 5,930,753 A | 7/1999 | Potamianos et al. |
| 5,943,421 A | 8/1999 | Grabon |
| 5,943,429 A | 8/1999 | Handel |
| 5,978,801 A | 11/1999 | Yuasa |
| 5,991,881 A | 11/1999 | Conklin et al. |
| 5,995,963 A | 11/1999 | Nanba et al. |
| 6,023,760 A | 2/2000 | Karttunen |
| 6,028,939 A | 2/2000 | Yin |
| 6,044,407 A | 3/2000 | Jones et al. |
| 6,067,569 A | 5/2000 | Khaki et al. |
| 6,070,172 A | 5/2000 | Lowe |
| 6,073,160 A | 6/2000 | Grantham et al. |
| 6,105,067 A | 8/2000 | Batra |
| 6,134,551 A | 10/2000 | Aucsmith |
| 6,138,176 A | 10/2000 | McDonald et al. |
| RE36,946 E | 11/2000 | Diffie et al. |
| 6,147,976 A | 11/2000 | Shand et al. |
| 6,169,969 B1 | 1/2001 | Cohen |
| 6,175,874 B1 | 1/2001 | Imai et al. |
| 6,226,676 B1 | 5/2001 | Crump et al. |
| 6,279,113 B1 | 8/2001 | Vaidya |
| 6,317,795 B1 | 11/2001 | Malkin et al. |
| 6,336,150 B1 | 1/2002 | Ellis et al. |
| 6,370,645 B1 | 4/2002 | Lee |
| 6,377,942 B1 | 4/2002 | Hinsley et al. |
| 6,381,242 B1 | 4/2002 | Maher, III et al. |
| 6,389,532 B1 | 5/2002 | Gupta et al. |
| 6,397,259 B1 | 5/2002 | Lincke et al. |
| 6,397,335 B1 | 5/2002 | Franczek et al. |
| 6,412,000 B1 | 6/2002 | Riddle et al. |
| 6,430,272 B1 | 8/2002 | Maruyama et al. |
| 6,463,474 B1 | 10/2002 | Fuh et al. |
| 6,499,107 B1 | 12/2002 | Gleichauf et al. |
| 6,578,147 B1 | 6/2003 | Shanklin et al. |
| 6,704,816 B1 | 3/2004 | Burke |
| 6,711,558 B1 | 3/2004 | Indeck et al. |
| 6,765,918 B1 | 7/2004 | Dixon et al. |
| 6,772,345 B1 | 8/2004 | Shetty |
| 6,785,677 B1 | 8/2004 | Fritchman |
| 6,804,667 B1 | 10/2004 | Martin |
| 6,807,156 B1 | 10/2004 | Veres et al. |
| 6,877,044 B2 | 4/2005 | Lo et al. |
| 6,886,103 B1 | 4/2005 | Brustoloni et al. |
| 6,901,461 B2 | 5/2005 | Bennett |
| 6,944,168 B2 | 9/2005 | Paatela et al. |
| 6,978,223 B2 | 12/2005 | Milliken |
| 6,981,054 B1 | 12/2005 | Krishna |
| 7,019,674 B2 | 3/2006 | Cadambi et al. |
| 7,046,848 B1 | 5/2006 | Olcott |
| 7,093,023 B2 | 8/2006 | Lockwood et al. |
| 7,139,743 B2 | 11/2006 | Indeck et al. |
| 7,167,980 B2 | 1/2007 | Chiu |
| 7,181,437 B2 | 2/2007 | Indeck et al. |
| 7,181,608 B2 | 2/2007 | Fallon et al. |
| 7,224,185 B2 | 5/2007 | Campbell et al. |
| 7,225,188 B1 | 5/2007 | Gai et al. |
| 7,305,383 B1 | 12/2007 | Kubesh et al. |
| 7,305,391 B2 | 12/2007 | Wyschogrod et al. |
| 7,386,564 B2 | 6/2008 | Abdo et al. |
| 7,408,932 B2 | 8/2008 | Kounavis et al. |
| 7,411,957 B2 | 8/2008 | Stacy et al. |
| 7,461,064 B2 | 12/2008 | Fontoura et al. |
| 7,565,525 B2 | 7/2009 | Vorbach et al. |
| 2001/0052038 A1 | 12/2001 | Fallon et al. |
| 2001/0056547 A1 | 12/2001 | Dixon |
| 2002/0069370 A1 | 6/2002 | Mack |
| 2002/0095512 A1 | 7/2002 | Rana et al. |
| 2002/0105911 A1 | 8/2002 | Pruthi et al. |
| 2002/0129140 A1 | 9/2002 | Peled et al. |
| 2002/0162025 A1 | 10/2002 | Sutton et al. |
| 2002/0166063 A1 | 11/2002 | Lachman et al. |
| 2003/0009693 A1 | 1/2003 | Brock et al. |
| 2003/0014662 A1 | 1/2003 | Gupta et al. |
| 2003/0018630 A1 | 1/2003 | Indeck et al. |
| 2003/0023876 A1 | 1/2003 | Bardsley et al. |
| 2003/0037037 A1 | 2/2003 | Adams et al. |
| 2003/0043805 A1 | 3/2003 | Graham et al. |
| 2003/0051043 A1 | 3/2003 | Wyschogrod et al. |
| 2003/0065607 A1 | 4/2003 | Satchwell |
| 2003/0065943 A1 | 4/2003 | Geis et al. |
| 2003/0074582 A1 | 4/2003 | Patel et al. |
| 2003/0110229 A1 | 6/2003 | Kulig et al. |
| 2003/0177253 A1 | 9/2003 | Schuehler et al. |
| 2003/0221013 A1 | 11/2003 | Lockwood et al. |
| 2004/0015633 A1 | 1/2004 | Smith |
| 2004/0028047 A1 | 2/2004 | Hou et al. |
| 2004/0049596 A1 | 3/2004 | Schuehler et al. |
| 2004/0054924 A1 | 3/2004 | Chuah et al. |
| 2004/0100977 A1 | 5/2004 | Suzuki et al. |
| 2004/0162826 A1 | 8/2004 | Wyschogrod et al. |
| 2004/0205149 A1 | 10/2004 | Dillon et al. |
| 2005/0005145 A1 | 1/2005 | Teixeira |
| 2005/0086520 A1 | 4/2005 | Dharmapurikar et al. |
| 2005/0175010 A1 | 8/2005 | Wilson et al. |
| 2005/0195832 A1 | 9/2005 | Dharmapurikar et al. |
| 2006/0031263 A1 | 2/2006 | Arrouye et al. |
| 2006/0036693 A1 | 2/2006 | Hulten et al. |
| 2006/0047636 A1 | 3/2006 | Mohania et al. |
| 2006/0053295 A1 | 3/2006 | Madhusudan et al. |
| 2006/0242123 A1 | 10/2006 | Williams, Jr. |
| 2006/0294059 A1 | 12/2006 | Chamberlain et al. |
| 2007/0011183 A1 | 1/2007 | Langseth et al. |
| 2007/0067108 A1 | 3/2007 | Buhler et al. |
| 2007/0078837 A1 | 4/2007 | Indeck et al. |
| 2007/0112837 A1 | 5/2007 | Houh et al. |
| 2007/0118500 A1 | 5/2007 | Indeck et al. |

| | | | |
|---|---|---|---|
| 2007/0130140 | A1 | 6/2007 | Cytron et al. |
| 2007/0174841 | A1 | 7/2007 | Chamberlain et al. |
| 2007/0179935 | A1* | 8/2007 | Lee et al. .............. 707/3 |
| 2007/0237327 | A1 | 10/2007 | Taylor et al. |
| 2007/0277036 | A1 | 11/2007 | Chamberlain et al. |
| 2008/0109413 | A1 | 5/2008 | Indeck et al. |
| 2008/0114724 | A1 | 5/2008 | Indeck et al. |
| 2008/0114725 | A1 | 5/2008 | Indeck et al. |
| 2008/0114760 | A1 | 5/2008 | Indeck et al. |
| 2008/0126320 | A1 | 5/2008 | Indeck et al. |
| 2008/0133453 | A1 | 6/2008 | Indeck et al. |
| 2008/0133519 | A1 | 6/2008 | Indeck et al. |

FOREIGN PATENT DOCUMENTS

| | | |
|---|---|---|
| EP | 0 851 358 A2 | 7/1998 |
| EP | 0 880 088 A2 | 11/1998 |
| EP | 0 887 723 A2 | 12/1998 |
| EP | 0 911 738 A2 | 4/1999 |
| JP | 9-269930 | 10/1997 |
| JP | 10-313341 | 11/1998 |
| JP | 2000357176 | 12/2000 |
| JP | 2001518724 | 10/2001 |
| WO | 9905814 | 2/1999 |
| WO | 9955052 | 10/1999 |
| WO | WO 01/22425 A1 | 3/2001 |
| WO | 0139577 | 6/2001 |
| WO | 0161913 | 8/2001 |
| WO | 0180558 | 10/2001 |
| WO | WO 01/80082 A2 | 10/2001 |
| WO | 02061525 | 8/2002 |
| WO | 02082271 | 10/2002 |
| WO | 03100650 | 4/2003 |
| WO | 03036845 | 5/2003 |
| WO | 2004017604 | 2/2004 |
| WO | 2004042560 | 5/2004 |
| WO | 2004042561 | 5/2004 |
| WO | 2004042562 | 5/2004 |
| WO | 2004042574 | 5/2004 |
| WO | 2005017708 | 2/2005 |
| WO | WO 2005 017708 A2 | 2/2005 |
| WO | 2005026925 | 3/2005 |
| WO | 2005048134 A | 5/2005 |
| WO | 2006023948 | 3/2006 |
| WO | 2006096324 | 9/2006 |

OTHER PUBLICATIONS

'Fast and scalable pattern matching for content filtering': Dharmapurikar, 2005, ACM, ANCS 05, pp. 183-192.*

Lancaster, Joseph M.; "Design and Evaluation of a BLAST Ungapped Extension Accelerator, Master's Thesis, May 2006"; Thesis (http://cse.seas.wustl.edu/Research/FileDownload.asp?489); 2006; Pages: Cover pp. 1-4; iii-x; pp. 1-65; Washington University in St. Louis.

Department of Computer Science & Engineering; "Technical Reports"; Publication (http://cse.seas.wustl.edu/Research/Publications.asp); Dec. 17, 2007; pp. 1-26; Washington University in St. Louis.

Herbordt et al.; "Single Pass, BLAST-Like, Approximate String Matching on FPGAs"; 14th Annual IEEE Symposium on Field-Programmable Custom Computing Machines (FCCM'06); Apr. 2006; pp. 1-10; IEEE.

International Search Report from the International Searching Authority for corresponding PCT/US2007/067319.

Anonymous, "Method for Allocating Computer Disk Space to a File of Known Size," IBM Technical Disclosure Bulletin, vol. 27, No. IOB, Mar. 1, 1985, New York.

Arnold et al., "The Splash 2 Processor and Applications", Proceedings 1993 IEEE International Conference on Cornputer Design: VLSI Iii Computers and Processors (ICCD '93); Oct. 3, 1993; pp. 482-485; IEEE Computer Society; Cambridge, MA USA.

Baer, Computer Systems Architecture; 1990; pp. 262-265; Computer Science Press; Potomac, Maryland.

Berk, "JLex: A lexical analyzer generator for JavaTM", downloaded from http://www.cs.princeton.edu/~appel/modern/java/JLex/ in Jan. 2002, pp. 1-18.

Braun et al., "Layered Protocol Wrappers for Internet Packet Processing in Reconfigurable Hardware", Proceedings of Hot Interconnects 9 (Hotl-9) Stanford, CA, Aug. 22-24, 2001, pp. 93-97.

Choi et al., "Design of a Flexible Open Platform for High Performance Active Networks", Allerton conference, Campaign, II, 1999.

Cloutier et al., "VIP: An FPGA-Based Processor for Image Processing and Neural Networks", Proceedings of Fifth International Conference on Microelectronics for Neural Networks, Feb. 12, 1996; pp. 330-336; Los Alarnitos, California.

Compton et al., "Configurable Computing: A Survey of Systems and Software", Technical Report, Northwestern University, Dept. of BCE, 1999.

Ebeling et al., "RaPiD-Reconfigurable Pipelined Datapath", University of Washington, Dept. of Computer Science and Engineering, Sep. 23, 1996; Seattle, WA.

Franklin et al., "Assisting Network Intrusion Detection with Reconfigurable Hardware", Symposium on Field-Programmable Custom Computing Machines (FCCM 2002), Apr. 2002, Napa, California.

Fu et al., "The FPX KCPSM Module: An Embedded, Reconfigurable Active Processing Module for the Field Programmable Port Extender (FPX)", Washington University, Department of Computer Science, Technical Report WUCS-01-14, Jul. 2001, pp. 1-60.

Gunther et al., "Assessing Document Relevance with Run-Time Reconfigurable Machines", 1996; Proceedings, IEEE Symposium on Napa Valley, CA, Apr. 17, 1996, pp. 10-17.

Hayes, "Computer Architecture and Organization", Second Edition; 1988; pp. 448-459; McGraw-Hill, Inc.

Hauck et al., "Software Technologies for Reconfigurable Systems", Northwestern University, Dept. of BCE, Technical Report, 1996, pp. 1-40.

Hezel et al., "FPGA-based Template Matching using Distance Transforms", Proceedings of the 10th Annual IEEE Symposium on Field-Programmable Custom Computing Machines (FCCM '02); Apr. 22, 2002; pp. 89-97; IEEE Computer Society, USA.

Hollaar, "Hardware Systems for Text information Retrieval", Proceedings of the Sixth Annual International ACM Sigir Conference on Research and Development in Information Retrieval; Jun. 6-8,1983: pp. 3-9; Baltimore, Mayland, USA.

Keutzer et al., "A Survey of Programmable Platforms-Network Proc", University of California-Berkeley, pp. 1-29.

Kulig et al., "System and Method for Controlling Transmission of Data Packets Over an Information Network", pending U.S. Patent Application.

Lin et al., "Real-Time Image Template Matching Based on Systolic Array Processor", International Journal of Electronics; Dec. 1, 1992; pp. 1165-1176; vol. 73, No. 6; London, Great Britain.

Lockwood et al., "Field Programmable Port Extender (FPX) for Distributed Routing and Queuing", ACM International Symposium on Field Programmable Gate Arrays (FPGA '2000), Monterey, CA, Feb. 2000, pp. 1-8.

Lockwood et al., "Hello, World: A Simple Application for the Field Programmable Port Extender (FPX)", Washington University, Department of Computer Science, Technical Report WUCS-TM-00-12, Jul. 11, 2000, pp. 1-14.

Lockwood et al., "Parallel FPGA Programmable over Backplane Chassis", Washington University, Department of Computer Science, Technical Report WUCS-TM-00-11, Jun. 12, 2000, pp. 1-12.

Lockwood et al., "Reprogrammable Network Packet Processing on the Field Programmable Port Extender (FPX)", ACM International Symposium on Field Programmable Gal Arrays (FPGA '2001), Monterey, Ca, Feb. 2001, pp. 87-93.

Lockwood, "An Open Platform for Development of Network Processing Modules in Reprogrammable Hardware", IEG DesignCon 2001, Santa Clara, CA, Jan. 2001, Paper WB-19, pp. 1-10.

Lockwood, "Building Networks with Reprogrammable Hardware", Field Programmable Port Extender (FPX); Jan. 2002 Gigabit Workshop Tutorial, Washington University, St. Louis, MO, Jan. 3-4, 2002.

Lockwood, "Evolvable Internet Hardware Platforms", NASA/DoD Workshop on Evolvable Hardware (EHW'01), Long Beach, CA, Jul. 12-14, 2001, pp. 1-9.

Lockwood, "Hardware Laboratory Configuration", Field Programmable Port Extender: Jan. 2002 Gigabit Workshop Tutorial,,Washington University, St. Louis, MO, Jan. 3-4, 2002.

Lockwood, "Introduction", Field Programmable Port Extender: Jan. 2002 Gigabit Workshop Tutorial, Washington University, St. Louis, MO, Jan. 3-4, 2002.

Lockwood, "Platform and Methodology for Teaching Design of Hardware Modules in Internet Routers and Firewalls", IEEE Computer Society International Conference on Microelectronic Systems Education (MSE'2001), Las Vega, NV, Jun. 17-18, 2001, pp. 56-57.

Lockwood, "Protocol Processing on the FPX", Field Programmable Port Extender. Jan. 2002 Gigabit Workshop Tutorial, Washington University, St. Louis, MO, Jan. 3-4, 2002.

Lockwood, "Simulation and Synthesis", Field Programmable Port Extender (FPX); Jan. 2002 Gigabit Workshop Tutorial, Washington University, St. Louis, MO, Jan. 3-4, 2002.

Lockwood, "Simulation of the Hello World Application for the Field-Programmable Port Extender (FPX)", Washington University, Applied Research Lab, Spring 2001 Gigabits Kits Workshop.

"Lucent Technologies Delivers 'PayloadPlus' Network Processors for Programmable, MultiProtocol, OC-48c Processing", Lucent Technologies Press Release, downloaded from http://www.lucent.comlpress/1000/0010320.meb.html on Mar. 21, 2002.

Mosanya et al., "A FPGA-Based Hardware Implementation of Generalized Profile Search Using Online Arithmetic", ACM/Sigda International Symposium on Field Programmable Gate Arrays (FPGA '99); Feb. 21-23, 1999; pp. 101-111; Monterey, CA, USA.

Moscola et al., "FPGrep and FPSed: Regular Expression Search and Substitution for Packet Streaming in Field Programmable Hardware", unpublished, pp. 1-19.

Nunez et al., "The X-MatchLITE FPGA-Based Data Compressor", Buromicro Conference 1999, Proceedings, Italy, Sep. 8-10, 1999, Los Alamitos, CA, pp. 126-132.

"Overview, Field Programmable Port Extender: Jan. 2002 Gigabit Workshop Tutorial", Washington University, St. Louis, MO, Jan. 3-4, 2002, pp. 1-4.

Annex to Form PCT/ISA/206, Communication Relating to the Results of the Partial International Search for PCT/US 03/15638; Feb. 3, 2004.

Patent Cooperation Treaty; International Search Report for PCT/US 03/15638; mail date: May 6, 2004.

Patent Cooperation Treaty; International Search Report for PCT/US2004/016398; mail date: Apr. 12, 2005.

Patent Cooperation Treaty; International Search Report for PCT/US 01/11255; mail date: Jul. 10, 2003.

"Payload Plus Agere System Interface," Agere Systems Product Brief, Jun. 2001, downloaded from Internet, Jan. 2002, pp. 1-6.

Pramanik et al., "A Hardware Pattern Matching Algorithm on a Dataflow", Computer Journal; Jul. 1, 1985; pp. 264-269; vol. 28, No. 3; Oxford University Press, Surrey, Great Britain.

Ratha et al., "Convolution on Splash 2", Proceedings of IEEE Symposium on FPGAS for Custom Computing Machines, Apr. 19, 1995; pp. 204-213; Los Alamitos, California.

Schmit, "Incremental Reconfiguration for Pipelined Applications", Dept. of ECE, Carnegie Mellon University 1997, Pittsburgh, PA, pp. 47-55.

Shah, "Understanding Network Processors", Version 1.0, University of California-Berkeley, Sep. 4, 2001.

Shirazi et al. "Quantitative Analysis of FPGA-based Database Searching", Journal of VLSI Signal Processing Systems For Signal, Image, and Video Technology; May 2001; pp. 85-96; vol. 28, No. 1/2; Kluwer Academic Publishers; Dordrecht, NL.

Sidhu et al., "Fast Regular Expression Matching using FPGAs", IEEE Symposium on Field Programmable Custom Computing Machines (FCCM 2001), Apr. 2001.

Sidhu et al., "String Matching on Multicontext FPGAs using Self-Reconfiguration", FPGA '99: Proceedings of the 1999 ACM/SIGDA 7th International Symposium on Field Programmable Gate Arrays, Feb. 1999, pp. 217-226.

Taylor et al., "Generalized RAD Module Interface Specification of the Field Programmable Port Extender (FPX) Version 2", Washington University, Department of Computer Science, Technical Report, Jan. 8, 2000, pp. 1-10.

Taylor et al., "Modular Design Techniques for the FPX", Field Programmable Port Extender, Jan. 2002 Gigabit WorkshopTutorial, Washington University, St. Louis, MO, Jan. 3-4, 2002.

"The Field-Programmable Port Extender (FPX)", downloaded from http://www.arl.wustl.edu/arl/ in Mar. 2002.

Villasenor et al., "Configurable Computing Solutions for Automatic Target Recognition", FPGAS for Custom Computing Machines, 1996,Proceedings, IEEE Symposium on Napa Valley, CA; Apr. 17-19, 1996; pp. 70-79; 1996 IEEE; .Napa Valley, CA, Los Alamitos, CA, USA.

Yamaguchi et al., "High Speed Homology Search with FPGAs", Proceedings Pacific Symposium on biocomputing; Jan. 3-7, 2002; pp. 271-282; vol. 7; Online; Lihue, Hawaii, USA.

Navarro, "A Guided Tour to Approximate String Matching", ACM Computing Surveys, vol. 33, No. 1, Mar. 2001, pp. 31-88.

Baeza-Yates and Navarro, "New and Faster Filters for Multiple Approximate String Matching", Random Structures and Algorithms (RSA) vol. 20, No. 1, Jan. 2002, pp. 23-49.

Taylor, "Models, Algorithms, and Architectures for Scalable Packet Classification", doctoral thesis, Department of Computer Science and Engineering, Washington University, St. Louis, MO Aug. 2004.

Taylor and Turner, "Scalable Packet Classification using Distributed Crossproducting of Field Labels", Proceedings of IEEE Infocom vol. 20, No. 1, Mar. 2005, pp. 1-12.

Ramakrishna et al., "A Performance Study of Hashing Functions for Hardware Applications", Journal of Computing and Information, vol. 1, No. 1, May 1994, pp. 1621-1636.

"RFC793: Transmission Control Protocol, Darpa Internet Program, Protocol Specification", Sep. 1981.

Anerousis et al., "Using the AT&T Labs PacketScope for Internet Measurement, Design, and Performance Analysis", Network and Distributed Systems Research Laboratory, AT&T Labs-Research, Florham, Park, NJ, Oct. 1997.

Artan et al., "Multi-packet Signature Detection using Prefix Bloom Filters", 2005, IEEE, pp. 1811-1816.

Baboescu et al., "Scalable Packet Classification".

Bloom, "Space/Time Trade-offs in Hash Coding With Allowable Errors", Communications of the ACM, Jul. 1970, pp. 422-426, vol. 13, No. 7, Computer Usage Company, Newton Upper Falls, Massachusetts, USA.

Chaney et al., "Design of a Gigabit ATM Switch", Washington University, St. Louis.

Cuppu and Jacob, "Organizational Design Trade-Offs at the DRAM, Memory Bus and Memory Controller Level: Initial Results," Technical Report UMB-SCA-1999-2, Univ. of Maryland Systems & Computer Architecture Group, Nov. 1999, pp. 1-10.

Dharmapurikar et al., "Deep Packet Inspection Using Parallel Bloom Filters," Symposium on High Performance Interconnects (Hotl), Stanford, California, 2003, pp. 44-51.

Dharmapurikar et al., "Longest Prefix Matching Using Bloom Filters," SIGCOMM, 2003, pp. 201-212.

Dharmapurikar et al., "Robust TCP Stream Reassembly in the Presence of Adversaries", Proc. of the 14th Conference on USENIX Security Symposium—vol. 14, 16 pages, Baltimore, MD, 2005; http://www.icir.org/vern/papers/TCPReassembly/TCPReassembly.pdf.

Feldmann, "BLT: Bi-Layer Tracing of HTTP and TCP/IP", AT&T Labs-Research, Florham Park, NJ, USA.

Gupta et al., "Packet Classification on Multiple Fields", Computer Systems Laboratory, Stanford University, Stanford, CA.

Gurtov, "Effect of Delays on TCP Performance", Cellular Systems Development, Sonera Corporation.

International Search Report for PCT/US2002/033286; Jan. 22, 2003.

International Search Report for PCT/US2005/030046; Sep. 25, 2006.

Jacobson et al., "RFC 1072: TCP Extensions for Long-Delay Paths", Oct. 1988.

Jacobson et al., "tcpdump—dump traffic on a network".

Johnson et al., "Pattern Matching in Reconfigurable Logic for Packet Classification", College of Computing, Georgia Institute of Technology, Atlanta, GA.

Madhusudan, "Design of a System for Real-Time Worm Detection", Hot Interconnects, pp. 77-83, Stanford, CA, Aug. 2004, found at http://www.hoti.org/hoti12/program/papers/2004/paper4.2.pdf.

Madhusudan, "Design of a System for Real-Time Worm Detection", Master's Thesis, Washington Univ., Dept. of Computer Science and Engineering, St. Louis, MO, Aug. 2004.

Madhusudan, "Design of a System for Real-Time Worm Detection", Power Point Presentation in Support of Master's Thesis, Washington Univ., Dept. of Computer Science and Engineering, St. Louis, MO, Aug. 2004.

Mao et al., "Cluster-based Online Monitoring System of Web Traffic", Dept. of Computer Science and Technology, Tsinghua Univ., Bejing, 100084 P.R. China.

Moscola et al., "FPSed: A Streaming Content Search-And-Replace Module for an Internet Firewall", Proc. of Hot Interconnects, 11th Symposium on High Performance Interconnects, pp. 122-129, Aug. 20, 2003.

Moscola, "FPGrep and FPSed: Packet Payload Processors for Managing the Flow of Digital Content on Local Area Networks and the Internet", Master's Thesis, Sever Institute of Technology, Washington University, St. Louis, MO, Aug. 2003.

Necker et al., "TCP-Stream Reassembly and State Tracking in Hardware", School of Electrical and Computer Engineering, Georgia Institute of Technology, Atlanta, GA.

Prakash et al., "OC-3072 Packet Classification Using BDDs and Pipelined SRAMs", Department of Electrical and Computer Engineering, The University of Texas at Austin.

Roberts, "Internet Still Growing Dramatically Says Internet Founder", Press Release, Caspian Networks, Inc.—Virtual Pressroom.

Schuehler et al., "Architecture for a Hardware Based, TCP/IP Content Scanning System", IEEE Micro, 24(1):62-69, Jan.-Feb. 2004, USA.

Schuehler et al., "TCP-Splitter: A TCP/IP Flow Monitor in Reconfigurable Hardware", Hot Interconnects 10 (Hotl-10), Stanford, CA, Aug. 21-23, 2002, pp. 127-131.

Shalunov et al., "Bulk TCP Use and Performance on Internet 2".

Singh et al., "The EarlyBird System for Real-Time Detection on Unknown Worms", Technical report CS2003-0761, Aug. 2003.

Taylor et al., "Dynamic Hardware Plugins (DHP): Exploiting Reconfigurable Hardware for High-Performance Programmable Routers", Computer Networks, 38(3): 295-310 (16), Feb. 21, 2002, and online at http://www.cc.gatech.edu/classes/AY2007/cs8803hpc_fall/papers/phplugins.pdf.

Waldvogel et al., "Scalable High-Speed Prefix Matching".

Weaver et al., "Very Fast Containment of Scanning Worms", Proc. USENIX Security Symposium 2004, San Diego, CA, Aug. 2004, located at http://www.icsi.berkely.edu/~nweaver/containment/containment.pdf.

Wooster et al., "HTTPDUMP Network HTTP Packet Snooper", Apr. 25, 1996.

Yan et al., "Enhancing Collaborative Spam Detection with Bloom Filters", 2006, IEEE, pp. 414-425.

"A Reconfigurable Computing Model for Biological Research Application of Smith-Waterman Analysis to Bacterial Genomes" A White Paper Prepared by Star Bridge Systems, Inc. [retrieved Dec. 12, 2006]. Retrieved from the Internet: <URL: http://www.starbridgesystems.com/resources/whitepapers/Smith%20Waterman%20Whitepaper.pdf.

Aldwairi et al., "Configurable String Matching Hardware for Speeding up Intrusion Detection", SIRARCH Comput. Archit. News, vol. 33, No. 1, pp. 99-107, Mar. 2005.

Altschul et al., "Basic Local Alignment Search Tool", J. Mol. Biol., Oct. 5, 1990, 215, pp. 403-410.

Baker et al., "High-throughput Linked-Pattern Matching for Intrusion Detection Systems", ANCS 2005: Proceedings of the 2005 Symposium on Architecture for Networking and Communications Systems, pp. 193-202, ACM Press, 2005.

Behrens et al., "BLASTN Redundancy Filter in Reprogrammable Hardware," Final Project Submission, Fall 2003, Department of Computer Science and Engineering, Washington University.

Cavnar et al., "N-Gram-Based Text Categorization", Proceedings of SDAIR-94, 3rd Annual Symposium on Document Analysis and Information Retrieval, Las Vegas, pp. 161-175, 1994.

Chamberlain et al., "Achieving Real Data Throughput for an FPGA Co-Processor on Commodity Server Platforms", Proc. of 1st Workshop on Building Block Engine Architectures for Computers and Networks, Oct. 2004, Boston, MA.

Chenna et al., "Multiple Sequence Alignment with the Clustal Series of Programs", Nucleic Acids Research, 2003, vol. 31, No. 13, pp. 3497-3500.

Cho et al., "Deep Packet Filter with Dedicated Logic and Read Only Memories", 12th Annual IEEE Symposium on Field-Programmable Custom Computing Machines, Apr. 2004.

Clark et al., "Scalable Pattern Matching for High Speed Networks", Proceedings of the 12th Annual IEEE Symposium on Field-Programmable Custom Computing Machines, 2004; FCCM 2004, Apr. 20-23, 2004; pp. 249-257; IEEE Computer Society; Cambridge, MA USA.

Compton et al., "Reconfigurable Computing: A Survey of Systems and Software", Technical Report, Northwestern University, Dept. of ECE, 1999, presented by Yi-Gang Tai.

Cong et al., "An Optional Technology Mapping Algorithm for Delay Optimization in Lookup-Table Based FPGA Designs", IEEE, 1992, pp. 48-53.

Denoyer et al., "HMM-based Passage Models for Document Classification and Ranking", Proceedings of ECIR-01, 23rd European Colloquim Information Retrieval Research, Darmstatd, DE, pp. 126-135, 2001.

Dharmapurikar et al., "Deep Packet Inspection Using Parallel Bloom Filters," IEEE Micro, Jan.-Feb. 2004, vol. 24, Issue: 1, pp. 52-61.

Edgar, "Muscle: Multiple Sequence Alignment with High Accuracy and High Throughput", Nucleic Acids Research, 2004, vol. 32, No. 5, pp. 1792-1797.

Forgy, "RETE: A fast algorithm for the many pattern/many object pattern matching problem", Artificial Intelligence, 19, pp. 17-37, 1982.

Franklin et al., "An Architecture for Fast Processing of Large Unstructured Data Sets." Proc. of 22nd Int'l Conf. on Computer Design, Oct. 2004, pp. 280-287.

Gavrila et al., "Multi-feature Hierarchical Template Matching Using Distance Transforms", IEEE, Aug. 16-20, 1998, vol. 1, pp. 439-444.

Guerdoux-Jamet et al., "Systolic Filter for Fast DNA Similarity Search", IEEE, 1995, pp. 145-156.

Gyang, "NCBI BLASTN Stage 1 in Reconfigurable Hardware," Technical Report WUCSE-2005-30, Aug. 2004, Department of Computer Science and Engineering, Washington University, St. Louis, MO.

Halaas et al., "A Recursive MISD Architecture for Pattern Matching", IEEE Transactions on Very Large Scale Integration, vol. 12, No. 7, pp. 727-734, Jul. 2004.

Hutchings et al., "Assisting Network Intrusion Detection with Reconfigurable Hardware", FCCM 2002: 10th Annual IEEE Symposium on Field-Programmable Custom Computing Machines, 2002.

Jeanmougin et al., "Multiple Sequence Alignment with Clustal X", TIBS, 1998, vol. 23, pp. 403-405.

Jones et al., "A Probabilistic Model of Information Retrieval: Development and Status", Information Processing and Management, Aug. 1998, 76 pages.

Krishnamurthy et al., "Biosequence Similarity Search on the Mercury System", Proceedings of the 15th IEEE International Conference on Application-Specific Systems, Architectures, and Processors (ASAP04), Sep. 2004, pp. 365-375.

Lancaster et al., "Acceleration of Ungapped Extension in Mercury BLAST", Seventh (7th) Workshop on Media and Streaming Processors, Nov. 12, 2005, Thirty-Eighth (38th) International Symposium on Microarchitecture (MICRO-38), Barcelona, Spain.

Ramakrishna et al., "Efficient Hardware Hashing Functions for High Performance Computers", IEEE Transactions on Computers, Dec. 1997, vol. 46, No. 12.

Ratha et al., "FPGA-based coprocessor for text string extraction", IEEE, Sep. 11-13, 2000, pp. 217-221.

Roesch, "Snort—Lightweight Intrusion Detection for Networks", Proceedings of LISA '99: 13th Systems Administration Conference; Nov. 7-12, 1999; pp. 229-238; USENIX Association, Seattle, WA USA.

Roy, "A bounded search algorithm for segmented channel routing for FPGA's and associated channel architecture issues", IEEE, Nov. 11, 1993, pp. 1695-1705, vol. 12.

Sourdis and Pnevmatikatos, "Fast, Large-Scale String Match for a 10Gbps FPGA-based Network Intrusion Detection System", 13th International Conference on Field Programmable Logic and Applications, 2003.

Steinbach et al., "A Comparison of Document Clustering Techniques", KDD Workshop on Text Mining, 2000.

Tan et al., "A High Throughput String Matching Architecture for Intrusion Detection and Prevention", ISCA 2005: 32nd Annual International Symposium on Computer Architecture, pp. 112-122, 2005.

Thompson et al., "The Clustal_X Windows Interface: Flexible Strategies for Multiple Sequence Alignment Aided by Quality Analysis Tools", Nucleic Acids Research, 1997, vol. 25, No. 24, pp. 4876-4882.

Uluski et al., "Characterizing Antivirus Workload Execution", SIGARCH Comput. Archit. News, vol. 33, No. 1, pp. 90-98, Mar. 2005.

Ward et al., "Dynamically Reconfigurable Computing: A Novel Computation Technology with Potential to Improve National Security Capabilities", May 15, 2003, A White Paper Prepared by Star Bridge Systems, Inc. [retrieved Dec. 12, 2006]. Retrieved from the Internet: <URL: http://www.starbridgesystems.com/resources/whitepapers/Dynamically%20Reconfigurable%20Computing.pdf.

"Technology Overview", downloaded from the http://www.datasearchsystems.com/tech.htm on Apr. 19, 2004.

Chamberlain et al., "The Mercury System: Embedding Computation Into Disk Drives", 7th High Performance Embedded Computing Workshop, Sep. 2003, Boston, MA.

Chamberlain et al., "The Mercury System: Exploiting Truly Fast Hardware for Data Search", Proc. of Workshop on Storage Network Architecture and Parallel I/Os, Sep. 2003, New Orleans, LA.

Office Action for EP Application No. 07761209.1 dated Jul. 21, 2009.

Office Action for U.S. Appl. No. 11/359,285 dated Sep. 4, 2009.

West et al., "An FPGA-Based Search Engine for Unstructured Database", Proc. of 2nd Workshop on Application Specific Processors, Dec. 2003, San Diego, CA.

* cited by examiner

METHOD AND APPARATUS FOR APPROXIMATE PATTERN MATCHING

FIELD OF THE INVENTION

The present invention relates to the field of approximate pattern matching with a large set of patterns. In particular, the present invention relates to a scalable filtering circuit and reduction stage for approximate pattern matching with a large group of patterns.

BACKGROUND OF THE INVENTION

Approximate pattern or string matching is a significant problem that arises in many important applications. These can include, but are not limited to, computational biology, databases and computer communications. This task includes searching for matches between the specified pattern or set of patterns while typically permitting a specified number of errors. As an example, one may desire to search for the word "queuing" while allowing for two errors. This could return results such as the word "queueing" with one character insertion and "cueing" with one character substitution and one character deletion. By allowing a specified number of errors, this allows the search to catch typical spelling variations or errors and still find the desired pattern. Approximate pattern matching is not only a complex task but requires a tremendous amount of computer resources.

Typically, there is a fast filtering step that is followed by the verification step that performs the full approximate matching function. An example of this prior art filtering technique is shown by referring to FIG. 1 and is generally indicated by numeral 10. This typical approach is to slice a pattern "P", as indicated by numeral 12, into k+1 pattern pieces, which are a sequence of non-overlapping sub-patterns, and search for exact matches between the text and the pattern pieces. In this case, "k" is equal to the number of allowable errors, which is the maximum edit distance $ed(T_{i...j}, P)$, which is indicated in this nonlimiting example by the numeral two (2) as indicated by numeral 14.

A data string $T_{i...j}$ 16 is then analyzed for an occurrence of at least one substring of the data string 16 that matches at least one of the non-overlapping sub-patterns associated with pattern "P" 12. This approach relies on the following properties:

a. If string $S=T_{a...b}$ matches pattern P with at most k errors, and $P=p_1 \ldots p_j$ (a sequence of non-overlapping sub-patterns), then some sub-string of S matches at least one of the $p_i$'s with at most $\lfloor k/j \rfloor$ errors b. If there are character positions $i \leq j$ such that $ed(T_{i...j}, P) \leq k$, then $T_{j-m+1...j}$ includes at least m-k characters of P where m is the size of the pattern (in characters)

c. Therefore, if we slice P into k+1 pieces (non-overlapping sub-patterns), then at least one of the pieces must match exactly Therefore, if we slice "P" 12 by the total number of errors "k" 14 plus one (1) into non-overlapping sub-pattern pieces then at least one of the non-overlapping sub-pattern pieces must match exactly. As shown in the Example of FIG. 1, the data string $T_{i...j}$ 16 is divided into k+1 or three (3) pieces of non-overlapping sub-patterns. Therefore the three (3) pieces are "abra" indicated by numeral 18, "cada" indicated by numeral 20, and "bra" indicated by numeral 22. In this example, "cada" indicated by numeral 20 is an exact match with two errors where the letters "br" are replaced and the letter "b" is deleted.

There is a significant need for a fast and cost effective mechanism for pattern matching utilizing a substantial amount of input data with a considerable set of potentially matching patterns.

SUMMARY OF INVENTION

In one aspect of this invention, a method for inspecting a data stream for data segments matching one or more patterns each having a predetermined allowable error with at least one search engine is disclosed. This method includes filtering a data stream for a plurality of patterns of symbol combinations with a plurality of parallel filter mechanisms each configured to detect one or more patterns each with an associated allowable error, detecting a plurality of potential pattern piece matches with the plurality of parallel filter mechanisms, identifying a plurality of potentially matching patterns, each having an associated allowable error, from the plurality of parallel filter mechanisms, reducing the identified plurality of potentially matching patterns to a set of potentially matching patterns, each having an associated allowable error with a reduction stage, providing associated data and the reduced set of potentially matching patterns, each having an associated allowable error, to a verification stage, and verifying presence of a pattern match in the data stream from the plurality of patterns of symbol combinations and associated allowable errors with the verification stage that includes an approximate match engine utilizing the associated data and the reduced set of potentially matching patterns.

In another aspect of this invention, a method for inspecting a data stream for data segments matching one or more patterns each having a predetermined allowable error with at least one search engine is disclosed. This method includes filtering a data stream for a plurality of patterns of symbol combinations with a plurality of parallel filter mechanisms each configured to detect one or more patterns each with an associated allowable error, wherein the plurality of parallel filter mechanisms is a group consisting of a set of parallel Bloom filters, a set of parallel Bloom filter arrays or a set of parallel Bloom filter arrays that utilize a single hash key generator, detecting a plurality of potential pattern piece matches with the plurality of parallel filter mechanisms, identifying a plurality of potentially matching patterns, each having an associated allowable error, from the plurality of parallel filter mechanisms, reducing the identified plurality of potentially matching patterns to a set of potentially matching patterns, each having an associated allowable error, providing associated data and the reduced set of potentially matching patterns, each having an associated allowable error, to a verification stage, and verifying presence of a pattern match in the data stream from the plurality of patterns of symbol combinations and associated allowable errors with the verification stage that includes an approximate match engine utilizing the associated data and the reduced set of potentially matching patterns.

In still another aspect of this invention, a method and system for inspecting a data stream for data segments matching one or more patterns each having a predetermined allowable error with at least one search engine is disclosed. This method includes utilizing a single hash key generator for extracting a plurality of hash values from a single hash value for inspecting the data stream for data segments matching one or more pattern pieces with false positive errors with at least one search engine, and utilizing the plurality of hash values with a plurality of parallel Bloom filter arrays.

In yet another aspect of this invention, a system for inspecting a data stream for data segments matching one or more patterns each having a predetermined allowable error with at least one search engine is disclosed. This system includes a filter stage, which utilizes a plurality of parallel filter mechanisms each configured to detect one or more patterns, each with an associated allowable error, that filter a data stream for a plurality of patterns of symbol combinations and detect a plurality of potential pattern piece matches, and identify a plurality of potentially matching patterns, each having an associated allowable error, a reduction stage, which reduces the identified plurality of potentially matching patterns to a set of potentially matching patterns, each having an associated allowable error, and a verification stage, which includes an approximate match engine, that receives and utilizes associated data and the reduced set of potentially matching patterns and associated allowable errors to verify a presence of a pattern match in the data stream from the plurality of patterns of symbol combinations.

In yet another aspect of this invention, a system for inspecting a data stream for data segments matching one or more patterns each having a predetermined allowable error with at least one search engine is disclosed. The system includes a plurality of parallel filter mechanisms, wherein the plurality of parallel filter mechanisms is a group consisting of a set of parallel Bloom filters, a set of parallel Bloom filter arrays or a set of parallel Bloom filter arrays that utilize a single hash key generator, each configured to detect one or more patterns, each with an associated allowable error, that filter a data stream for a plurality of patterns of symbol combinations and detect a plurality of potential pattern piece matches and identify a plurality of potentially matching patterns, each having an associated allowable error, a reduction stage that reduces the identified plurality of potentially matching patterns to a set of potentially matching patterns, each having an associated allowable error, and a verification stage, which includes an approximate match engine, that receives and utilizes associated data and the reduced set of potentially matching patterns and associated allowable errors to verify a presence of a pattern match in the data stream from the plurality of patterns of symbol combinations.

Illustrative, but nonlimiting, examples of potential application of the present invention include: an intrusion detection system (IDS) for computer communication networks; computational biology and genetics; text searches for structured and unstructured text; and text searches from optical character scans (OCS).

Additional aspects of the present invention include, but are not limited to: a filtering technique for approximate matching with multiple patterns where each pattern may specify its allowable errors that can include a large number of pattern pieces, e.g., tens of thousands of patterns or more; utilizing a parallel set of exact match engines, one for each pattern piece length, to perform parallel match operations and to support a wide variety of (pattern length, allowable error) combinations; allowing each pattern to have a specified number of errors; amenability to parallel hardware search implementation and such implementation can provide fast search results; simplifying a verification stage by limiting the number of potentially matching patterns for a region of text, allowing the verification engine to process additional potential search results in a shorter period of time, which allows the total system to scale in capacity while operating at very high speeds; and utilizing a Bloom filter array for each exact match engine; and efficiently implementing each Bloom filter array by using only one hash function generator.

Still another aspect of present invention is the reduction stage wherein the scope of the search in the verification stage is reduced with a smaller set of possibly matching patterns.

These techniques use a layer of indirection between pieces and patterns which allows each pattern and its allowable errors to be stored only once. There is a first illustrative technique that simplifies the data structures, making them amenable to hardware implementation. This technique includes a lookup using a bin index to retrieve the piece identifiers for the potentially matching pieces. A second lookup uses the piece identifiers to retrieve the pattern identifiers for the patterns that include the pieces. A third lookup uses the pattern identifiers to retrieve the pattern and associated allowable error pairs to be considered by the verification engine. There is a second illustrative, but nonlimiting technique that utilizes the text pieces that produced matches in the exact match engines to resolve the pattern identifiers for the patterns that include the piece. The pattern identifiers are used to retrieve the pairs of patterns and associated allowable errors to be considered by the verification engine.

These are merely some of the innumerable aspects of the present invention and should not be deemed an all-inclusive listing of the innumerable aspects associated with the present invention.

BRIEF DESCRIPTION OF DRAWINGS

For a better understanding of the present invention, reference may be made to the accompanying drawings in which.

DETAILED DESCRIPTION OF THE INVENTION

Figure 1:
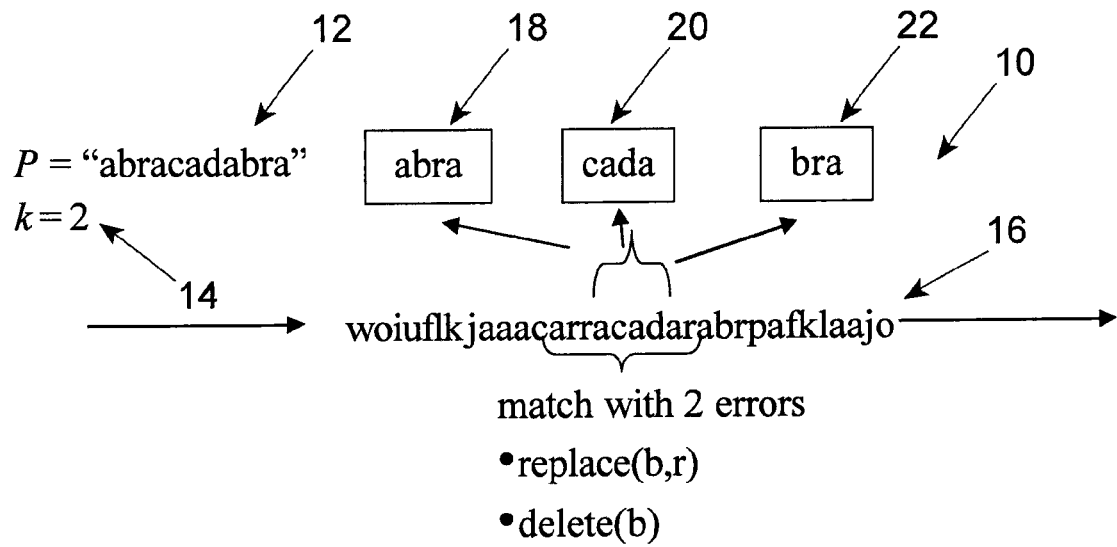
FIG. 1 provides an illustrative overview of a prior art approximate pattern matching technique.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to obscure the present invention.

The present invention is a scalable filtering circuit for approximate pattern matching with a large set of patterns. The filtering circuit checks for potential matches between a set of stored patterns, where each pattern specifies the number of allowable errors, and an input stream of characters. The number of allowable errors is predetermined or specified using the general edit distance measure that counts the number of single character additions, deletions, and substitutions. When a potential match is detected, the location or locations in the input data stream is identified as well as the matching pattern or plurality of potentially matching patterns. The present invention is designed to operate in concert with a verification stage that looks for an approximate match in the data segment(s) of the input data stream utilizing the previously identified potentially matching pattern(s) from the total number of potentially matching patterns.

The methodology for searching for a single pattern can be stated as follows: identifying instances of pattern "P" in text "T" with "k" allowable errors, where "k" is the maximum edit distance. The edit distance is defined as the number of single character insertions, deletions, and substitutions with all errors typically, but not necessarily share the same weighting. In general, other types of errors such as transpositions may be included in the distance measure and each type of error may be assigned a unique weight.

Assuming that "m" is the size of the pattern in characters and "n" is the size of the text in characters, then the error level can be defined for a particular pattern as the ratio of the number of allowable errors and the size of the pattern, which is "α=k/m". The error level and the size of the alphabet from which the pattern and text are constructed, "σ," affect the probability that matches will be found. An expression for the match probability, "f(m,k)" assuming a randomly constructed text and a randomly constructed pattern is provided by the following equation:

$$f(m,k) = \left(\frac{e^2}{\sigma(1-\alpha)^2}\right)^{m(1-\alpha)}$$

This is where "e" is the base of the natural logarithm.

It is believed that filtering algorithms achieve better performance for a variety of approximate pattern matching problems. The general approach being to perform a simple search on a small section of text to identify potential matches. When a potential match is found, the region of text is examined to see if it is, in fact, an approximate match for a specified pattern. In general, verification is performed by any approximate pattern matching algorithm and may be tightly or loosely coupled to a filtering operation.

Figure 2:
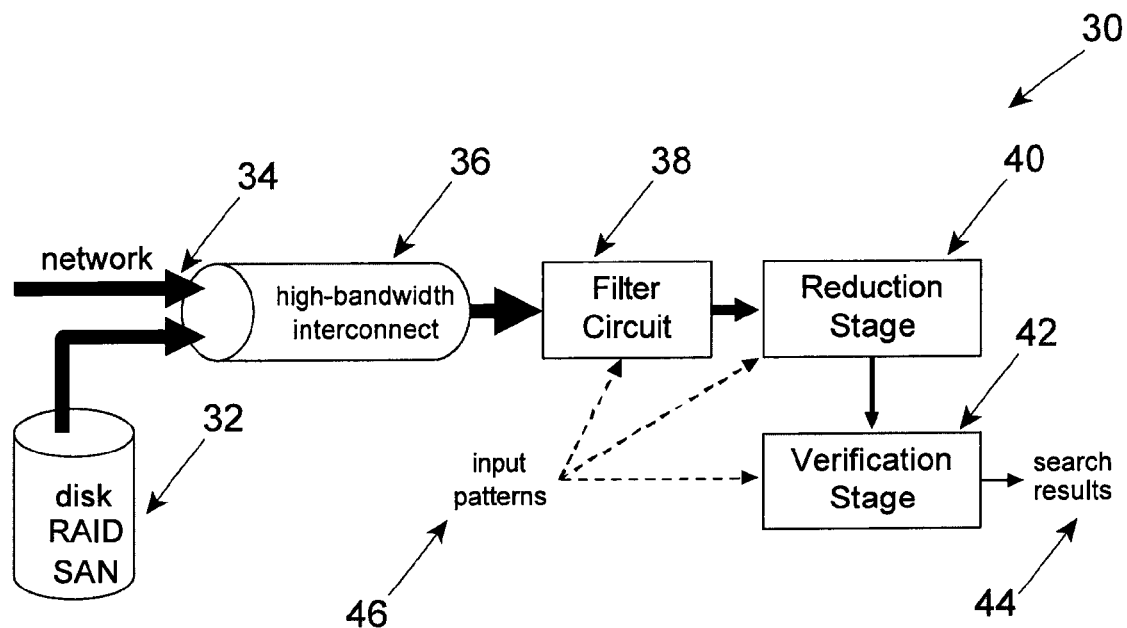
FIG. 2 provides an exemplary block diagram of the present invention including a data source, a filter circuit, a reduction stage and a verification stage.

A general schematic of the system of the present invention is shown in FIG. 2 and is indicated by numeral 30. Large amounts of data can be provided as input through either a communication link, a disk, a redundant array of independent disks (RAID), or storage area network (SAN), as well as a wide variety of other data sources capable of feeding a filter circuit with high data speed. This data input is indicated by numeral 32 can also be provided through a network input that is indicated by numeral 34. High speed data can be provided through a high-bandwidth interconnect indicated by numeral 36 at high speeds. This high speed data is then passed through a filter circuit 38 that scans the input data for potential matches for a set of input patterns. There is then a reduction stage 40 between the filter circuit 38 and a verification stage 42 that narrows the set of potentially matching patterns that must be considered by the verification stage 42 when processing data segments that produce a match in the filter circuit 38. The verification stage 42 performs a full approximate operation to verify whether or not there is a match for a set of input patterns 46. Search results are then provided as indicated by numeral 44. Predetermined input patterns 46 are provided to the filter circuit 38, the reduction stage 40 and the verification stage 42.

In a particular window of text, it is possible to search for an exact match and any of the pattern pieces specified by a predetermined number "r" patterns. If a specific pattern "i" allows "$k_i$" errors, then the total number of pattern pieces is indicated by the equation:

$$p = \sum_{i=1}^{r}(k_i + 1)$$

Figure 3:
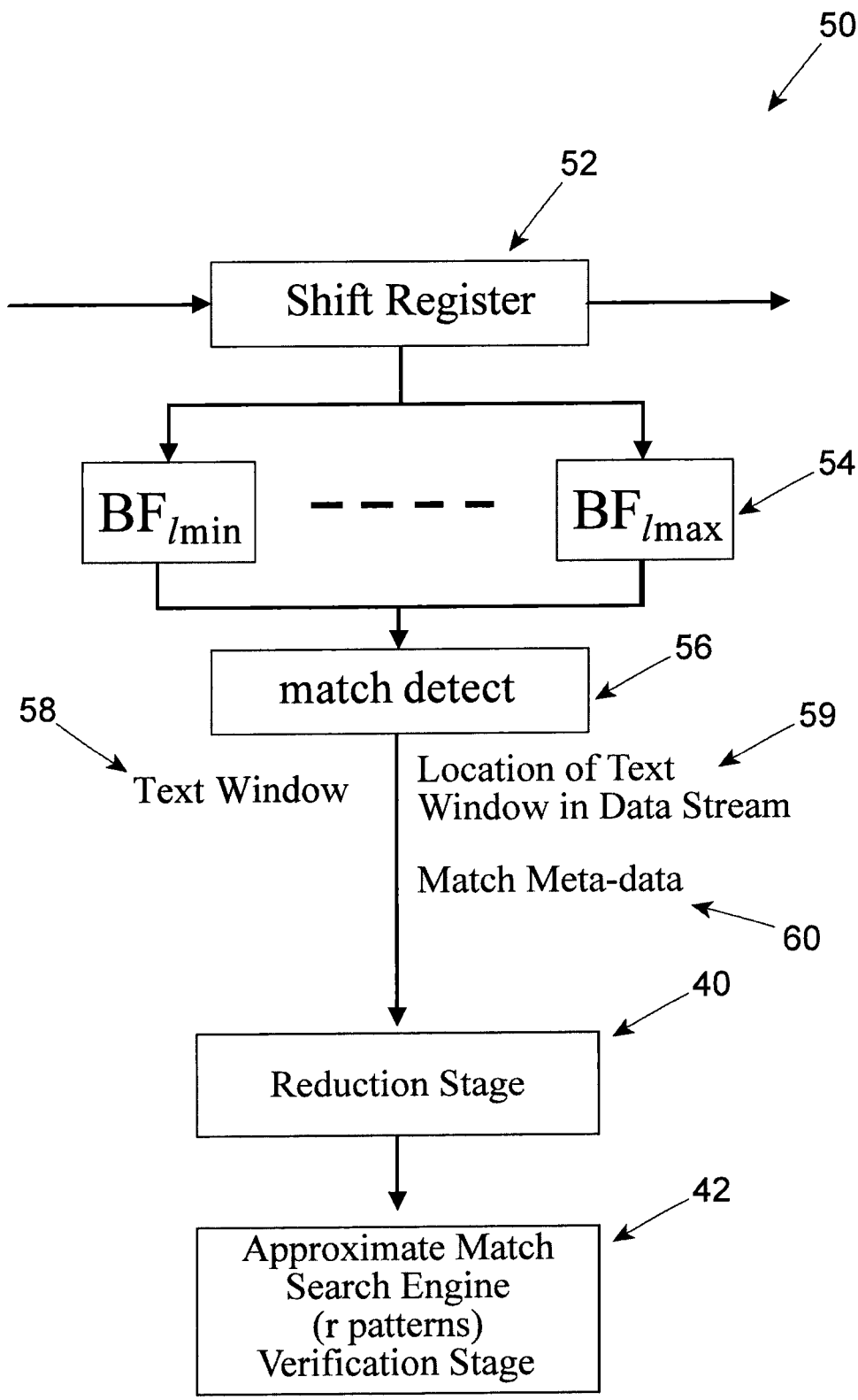
FIG. 3 is an illustrative, but nonlimiting, block diagram of the present invention including Bloom filters with a match detection function; a reduction stage and a verification stage having approximate pattern matching.

This filtering approach is utilized with parallel filter mechanisms which can include a parallel set of Bloom filters, a set of parallel Bloom filter arrays, or a set of Bloom filter arrays that utilize a single hash function generator. As shown in FIG. 3, which is the schematic of the basic hardware implementation of the present invention is indicated by numeral 50 and includes a number of Bloom filters indicated by numeral 54. In a classical Bloom filter 54, elements are inserted into a set using "b" hash values were the element is utilized as the key and where each hash value identifies a bit position in a B-bit vector. The bits at each of the b bit positions are preferably set to one (1). If a bit is already set to one (1), then no change will be made. In order to test whether or not a particular element is a member of the set represented by a Bloom filter 54, the element and the same b hash functions are utilized to compute b hash values. If all the b bits in the vector are set to one (1), then the element is declared to be a member of the set.

A Bloom filter 54 will not produce a false negative. If an element is a member of a set, then the b bit positions in the B-bit vector are set to one (1) when the element is inserted into the set. The insertion of additional elements in the set does not reset any of the bits in the vector. However, Bloom filters 54 do produce false positives with a determined probability. This probability can be computed by the equation:

$$f = \left(1 - e^{\frac{-pb}{B}}\right)^b$$

If the following relationship holds:

$$b = \frac{B}{p}\ln 2$$

then: $f = (1/2)^b$

Approximate match filtering on multiple patterns and allowing each pattern to specify its allowable errors produces sets of pattern pieces of various lengths. Preferably, but not necessarily, the bloom filters 54 store fixed-length elements with one bloom filter circuit 54 for each possible pattern piece length. Therefore, the range of possible pattern piece lengths are constrained within a range.

If $l_{min}$ is the minimum pattern piece length then $l_{min}$ is less than or equal to the value of the size of the pattern m divided by the maximum edit distance k plus one (1): TK2Z $$l_{min} \leq \left\lfloor \frac{m}{k+1} \right\rfloor$$

If $l_{max}$ is the maximum piece length, then $l_{max}$ is greater than or equal to the value of the size of the pattern m divided by the maximum edit distance k plus one (1):

$$\lceil \frac{m}{k+1} \rceil \leq l_{max}$$

The total number of Bloom filters 54 that are required when each Bloom filter of the Bloom filters 54 corresponds to a pattern piece length is:

$$l_{max} - l_{min} + \text{one} \tag{1}$$

A preferred approach is to query each of the Bloom filters 54 in parallel, as shown by the schematic provided by numeral 50 in FIG. 3. Each one of the Bloom filters 54 correspond to a pattern piece length so that various strides of the text window can be selected as an input key to each Bloom filter 54.

If any of the Bloom filters 54 result in a detected match 56, then the segment of data or text window 58, the location of the segment of data in the input stream 59 and additional match meta data 60 are sent to a reduction stage 40. The techniques utilized in the reduction stage 40 can narrow the potentially matching patterns significantly, e.g., over 10,000 to less than 10.

The result passing from the reduction stage 40 goes to the verification stage 42, which includes the approximate match search engine. By reducing the number of candidate patterns to be considered by the verification stage 42, allowing the verification stage to process more potential search results in a given amount of time, and thus allowing the total system to scale in capacity while operating at high speeds.

A Bloom filter array 54 typically minimizes the number of memory accesses, e.g., random access memory (RAM), required for a set membership query. Moreover, the Bloom filter array 54 partitions the B-bit vector into "W" vectors of size "q=B/W" where "q" is the word size of the memory. There can preferably be an even distribution of stored elements over the "W" vectors (memory words) using a pre-filter hash function. This creates an array of "W" "q"-bit Bloom filters.

Figure 4:
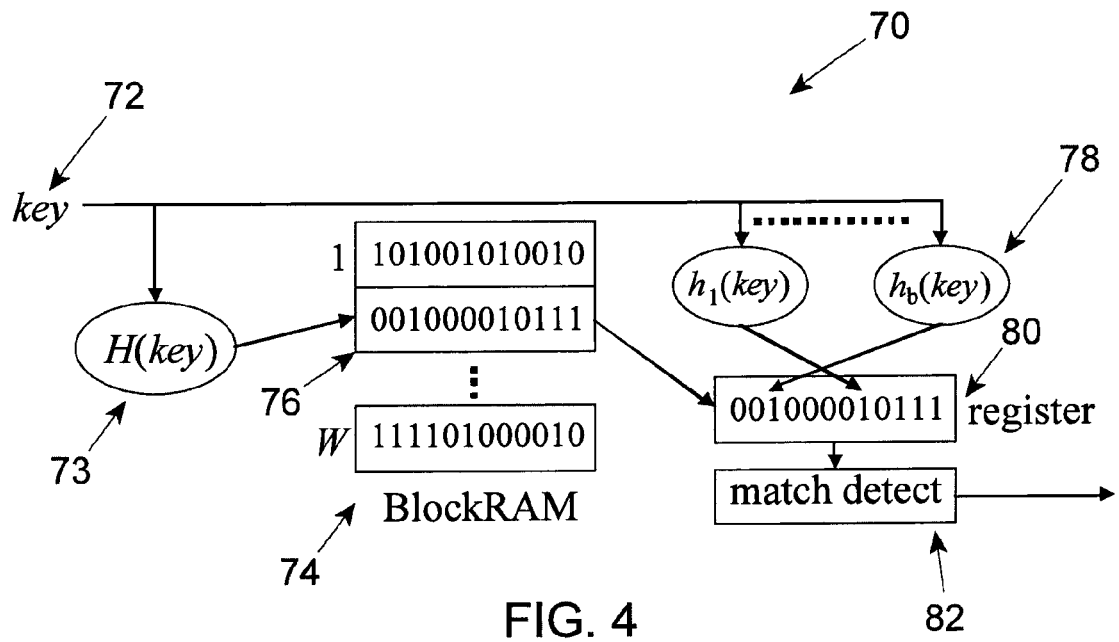
FIG. 4 provides an exemplary block diagram of a first filtering stage processing technique using a Bloom filter array.

The bits in the "q"-bit Bloom filters 54 are set, during programming, and then checked, during queries, using "b" hash functions. Querying a Bloom filter array 54 requires one (1) memory read to fetch the "q"-bit vector. Using a register 80 and bit-select circuitry 82, checking the bit locations specified by "b" hash functions may be performed on-chip, in a pipelined fashion, as shown in FIG. 4 and generally indicated by numeral 70.

In this application, a key (i.e. pattern piece) is indicated by numeral 72. The key is used by the pre-filter hash function 73 to identify a particular "q"-bit vector in the listing of "w" vectors. The particular "q"-bit vector in the listing of "w" vectors is indicated by column 74 in memory, e.g., RAM, wherein a particular and illustrative vector is identified by numeral 76. These queries are checked with series of "b" hash functions indicated by numeral 78 identifying bit positions within a register 80, which is then provided to a match detection function 82. If all "b" bit positions are set to a one (1), then the key is a pattern piece for a potentially matching pattern.

Figure 5:
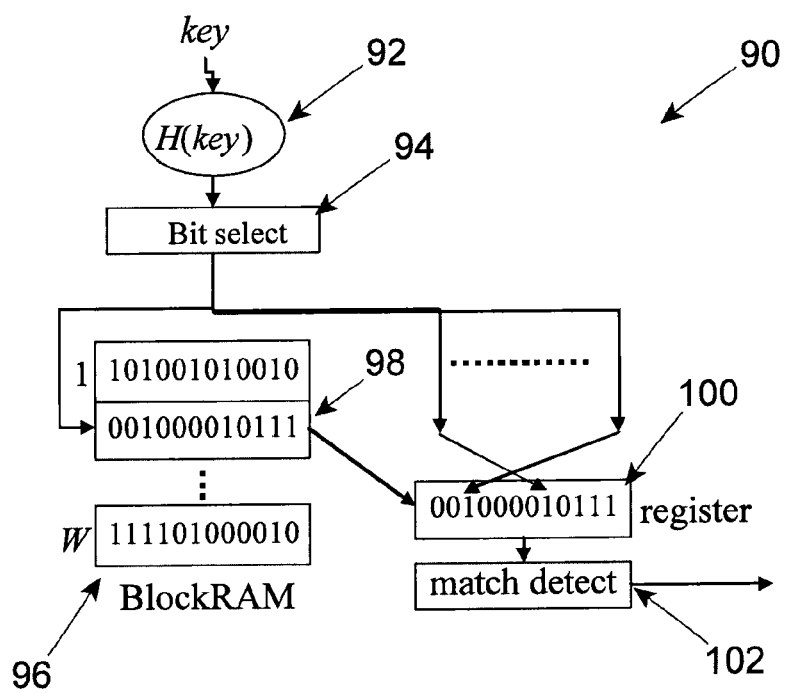
FIG. 5 provides an exemplary block diagram of a second filtering stage processing technique using a Bloom filter array with a single hash function generator.

Preferably, the amount of logic required to implement a Bloom filter array 54 can be minimized, as shown in FIG. 5. This logic is generally indicated by numeral 90. There is a single hash function indicated by numeral 92. There is the generation of a single random value. A subset of the bits from this random value are utilized to construct the pre-filter hash address and "b" filter bit-positions that is indicated by numeral 94. The particular "q"-bit vector in the listing of "w" vectors is indicated by column 96 in memory, e.g., RAM, wherein a particular and illustrative vector is identified by numeral 98. This particular vector 98 is passed to a register 100 and then on to a match pattern detection function 102. This Bit select value 94 must be at least $\log_2(W) + (b \cdot \log_2(q))$ bits in size. The $H_3$ class of hash functions 92 is an illustrative, but nonlimiting, example of hash functions that can produce wide enough values for this application.

An illustrated, but nonlimiting example of reconfigurable hardware that could be utilized includes FPGAs, i.e., field programmable gate arrays, which includes a Xilinx® VirtexII® 4000 series FPGA. Xilinx, Inc., is a Delaware corporation, having a place of business at 2100 Logic Drive, San Jose, Calif. 95124-3400. An illustrated, but nonlimiting, example of the embedded memory in the VirtexII® series of devices include One Hundred and Twenty (120) of the eighteen (18) kilobyte block random access memories (BlockRAMs). These BlockRAMs can be configured to various size words with an illustrative, but nonlimiting, maximum word length of thirty-six (36) bits by Five Hundred and Twelve (512) words.

Utilizing the previous expression for probability of a false positive and assuming uniform hashing performance, the Bloom filter array 54 implemented with an eighteen (18) kilobyte BlockRAM can represent a set of 3,194 elements with a false probability of 0.063 when the number of b bit positions equals four (4). When number of b bit positions equals three (3), the capacity increases to 4,259 elements but the false positive probability increases to 0.125.

As previously stated, one Bloom filter array 54 is required for each unique pattern piece length. There is also consideration of the number of parallel circuits that are required to keep pace with the data input rate. In an illustrative, but nonlimiting example, a system that accepts eight (8) new ASCII characters per cycle (64-bit interface) requires eight (8) instances of the circuit operating in parallel. For the VirtexII 4000® FPGA, there are at most fifteen (15) BlockRAMs available for each circuit instance. In order to have BlockRAM resources available for interface buffers, this results in limiting the BlockRAMs to a lower number, e.g., fourteen BlockRAMs. This illustrative, but nonlimiting, resource allocation can place a constraint on the length of pattern pieces and the combination of pattern piece and allowable error. This in turn places a limit on the maximum error level. When "m" is equal to the size of the pattern, "p" is equal to number of pattern pieces and "k" is the number of allowable errors or edit distance then the following equations are applicable:

$$m_{min} = p_{min}(k+1)$$

$$m_{max} = p_{max}(k+1)$$

$$\alpha_{max} = \frac{k}{m_{min}} = \frac{k}{p_{min}(k+1)}$$

where α=ratio of the number of errors divided by the size of the pattern.

The following Table 1 is when "α", i.e., ratio of the number of errors divided by the size of the pattern is less than or equal to one (1):

TABLE 1

| k | $m_{min}$ | $m_{max}$ |
|---|---|---|
| 0 | 1 | 14 |
| 1 | 2 | 28 |

TABLE 1-continued

| k | $m_{min}$ | $m_{max}$ |
|---|---|---|
| 2 | 3 | 42 |
| 3 | 4 | 56 |
| ... | ... | ... |

The following Table 2 is when "α", i.e., ratio of the number of errors divided by the size of the pattern is less than or equal to one-half (½):

TABLE 2

| k | $m_{min}$ | $m_{max}$ |
|---|---|---|
| 0 | 2 | 15 |
| 1 | 4 | 30 |
| 2 | 6 | 45 |
| 3 | 8 | 60 |
| ... | ... | ... |

The following Table 3 is when "α", i.e., ratio of the number of errors divided by the size of the pattern is less than or equal to one-third (⅓):

TABLE 3

| k | $m_{min}$ | $m_{max}$ |
|---|---|---|
| 0 | 3 | 16 |
| 1 | 6 | 32 |
| 2 | 9 | 48 |
| 3 | 12 | 64 |
| ... | ... | ... |

Therefore in the second example and Table 2, when "α", i.e., ratio of the number of errors divided by the size of the pattern is less than or equal to one-half (½) and when the errors, i.e., "k=0", there must be at least two (2) characters and no more than fifteen (15) characters. A pattern that allows one error, i.e., "k=1", must contain at least four (4) characters and no more than thirty (30) characters. Although a wide variety of admissible pattern sizes and allowable errors can be utilized, it is believed that a pattern is at least two (2) characters and no more than fifteen (15) characters will be a workable constraint for most text searches in English, however, this should not be construed as a limit.

A rough capacity estimate can be developed by assuming that pieces are uniformly distributed over a range of allowable lengths. In an illustrative, but nonlimiting example, if each Bloom filter array 54 has a capacity of approximately Three Thousand (3,000) pattern pieces then the system has an aggregate capacity of Forty-Two Thousand (42,000) pattern pieces. If it is assumed that each pattern can be divided into three (3) pattern pieces, then the system has a capacity of Fourteen Thousand (14,000) patterns.

Once a potential match has been detected one or more pattern piece lengths 56, as shown in FIG. 3, then the region of text must be examined by the verification stage 42 in order to determine whether or not there is an approximate match for one of the "r" patterns. Since "r" may be on the order of 10,000 patterns or more, there is a need to narrow the scope of the search that the verification stage 42 must perform. This is where the reduction stage 40 provides a valuable role of reducing the set of possible matching patterns (pattern set) for the verification stage 42 to consider. As long as the parameters fall within the constraints, there is an assumption that the number of allowable errors may be specified for each pattern.

Throughout this patent application as shown in FIG. 3, the filter stage 38, the reduction stage 40 and/or the verification stage 42, as shown in FIG. 3, can use at least one reconfigurable logic device, e.g., Field Programmable Gate Array ("FPGA") or at least one integrated circuit, e.g., Application-Specific Integrated Circuit ("ASIC").

There are two illustrative, but nonlimiting, approaches to perform the reduction stage 40. The first approach is to simplify data searches utilized to resolve the pattern set indicated by numeral 120 in FIG. 6. This allows a data string to come into a shift register 52, which then passes into a filter stage or circuit 38 that preferably includes a Bloom filter array 54. With this approach, the objective is to utilize some, if not all, of the hash values computed by the Bloom filter array 54 in the filter stage or circuit 38 as an index into a table 128, e.g., BinIndex 124.

For example a pattern piece 121 can be received by the filter stage or circuit 38 and is received as hash values 126 comprising the BinIndex 124. The entries in this first table 128 contain identifiers 127 for the pattern pieces, e.g., PieceIDs, which map to the hash values 126 comprising the BinIndex 124. For example, there is an illustrative identifier, e.g., PieceID$_1$ and PieceID$_4$, which is associated with the example pattern piece 121. The identifiers 127 for the pattern pieces, e.g., PieceIDs, are a unique binary tag assigned to each pattern piece.

There is a second table 132 that utilizes the identifiers 128 for the pattern pieces, e.g., PieceIDs, to index one or more pattern identifiers for the set of potentially matching patterns. Since one or more patterns may specify a particular pattern piece, the entries in the second table 132 contain one or more pattern identifiers, e.g., PIDs. Pattern identifiers, e.g., PIDs, are unique binary tags associated with each pattern. For example, with the illustrative identifier, 131, relates to two patterns 137 and 138.

There is a third table 134 that utilizes the pattern identifiers, e.g. PIDs, to index one or more (pattern, allowable error) pairs. The identified set or plurality of potentially matching patterns, each with predetermined allowable errors, e.g. (pattern, allowable error) pairs 137 and 138, is then created as indicated by numeral 136.

This pattern set of potential matches 136 is passed onto the verification stage 42, which includes evaluation by an approximate match engine 142 for matching patterns and associated predetermined allowable errors. There only needs to be one copy of tables for the pattern piece identifiers 128, e.g., PieceIDs, pattern identifiers 132, e.g., PIDs and patterns 134 so long as the number of lookups per cycle does not exceed the amount of lookups supported by the memories.

Figure 7:
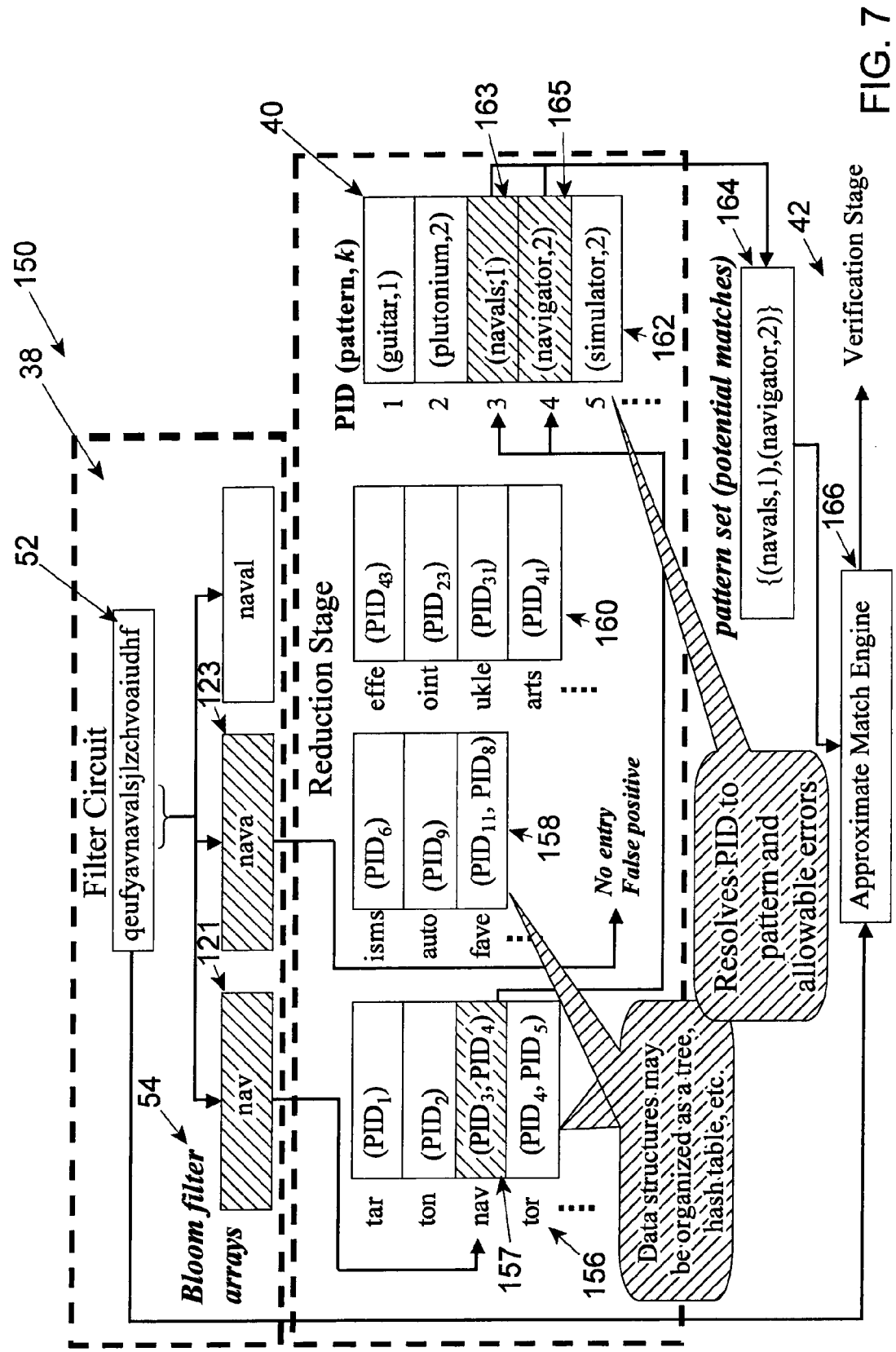
FIG. 7 provides an exemplary block diagram of a second reduction stage processing technique.

There is a second and preferred methodology for the reduction stage 40, which is generally indicated by numeral 150 in FIG. 7. This allows a data string to pass into a filter stage or circuit 38 that preferably includes a Bloom filter array 54. With this approach, actual data segments or pieces that produce a match in the Bloom filter array 54 are utilized to resolve the pattern identifiers for the patterns 162 that specify those pattern pieces. The data segments or pieces that produce a match are used to identify one or more entries in data structures, indicated by numerals 156, 158 and 160, which store pattern identifiers, e.g., PIDs, for the patterns that specify the associated pattern pieces. Illustrative, but nonlimiting examples of suitable data structures are a hash table and a balanced search tree. The methodology may include one or more data structures. In the illustrative, but nonlimiting example 150 in FIG. 7, one data structure is allocated for each pattern piece length.

In an illustrative, but nonlimiting example, two data segments or pieces that produce a match in the Bloom filter array 54 are identified by numerals 121 and 123. Data piece 121 identifies the entry 157 in the data structure as part of the reduction stage 40. These data structures 156, 158 and 160 can include a wide variety of different structures, e.g., decision tree, hash table, and so forth. The result of these lookup(s) is a set of pattern identifiers for the patterns in the pattern set. As with the prior approach, these pattern identifiers, e.g., PIDs, 156, 158 and 160 are utilized to retrieve patterns and associated allowable errors from a table 40 prior to a step of verification. The previously referenced entry 157 identify patterns 163 and 165 and associated allowable errors to produce a set of potential matches 164. The set of potential matches and associated predetermined allowable errors 164 is then evaluated by an approximate match engine 166 in the verification stage 42.

This approach resolves the set of pattern identifiers in a single step instead of two steps and also eliminates false positive errors produced by the Bloom filter arrays 54. Also, since the actual data segment is utilized to locate entries in the pattern identifier structure(s), an explicit match is performed. If there is no entry in the table, then a false positive is detected and no pattern identifiers, e.g., PIDs, are passed onto the verification stage 42 for that particular pattern piece length. The tradeoff is that the data structures can be more complex and the implementation more resource intensive depending on the implementation.

Therefore, this is a scalable design for a filtering circuit 38 and reduction stage 40 for approximate pattern matching on multiple patterns that are amenable to hardware implementation. In addition to the thousands of patterns, multiple filter circuits can support multiple input symbols per cycle. Utilizing the high performance filtering circuit 38 and the reduction stage 40, the performance requirements placed on a verification stage 40 can be analyzed. For the purpose of this analysis, we assume that all patterns specify the same number of allowable errors, "k". Effective load on the verification stage is determined as the probability of a match and the expected size of the set of potentially matching patterns. The probability of match is simply the sum of the probability that any of the "r(k+1)" pieces produce a match in a text window and the false positive probability of the Bloom filter arrays 54 where "r" is the predetermined number of "r" pattern pieces and "k" is the number of predetermined errors.

If "L" is the number of Bloom filter arrays 54 and assuming random text on an alphabet of "σ" characters, the probability of any of these pieces matching would be:

$$E[match] = \frac{r(k+1)}{\sigma^{\lfloor \frac{m}{k+1} \rfloor}}$$

The addition of the false positive probability of the Bloom filter arrays provides:

$$E[match] = \frac{r(k+1)}{\sigma^{\lfloor \frac{m}{k+1} \rfloor}} + Lf$$

By utilizing illustrative, but nonlimiting, example values L=14, σ=40, r=14,000 and f=0.0034, the match probability is highly sensitive to the minimum piece length. For example, when m=5 and k=1 (a minimum piece length of two (2) characters), then the match probability is one (1). If the pattern size is increased to six (6) (a minimum pattern piece length of three (3) characters), then the match probability is 0.079. This result suggests that the minimum pattern piece size should be three (3) characters or more. In this situation, there will be an expectation of one match every twelve (12) cycles.

Figure 6:
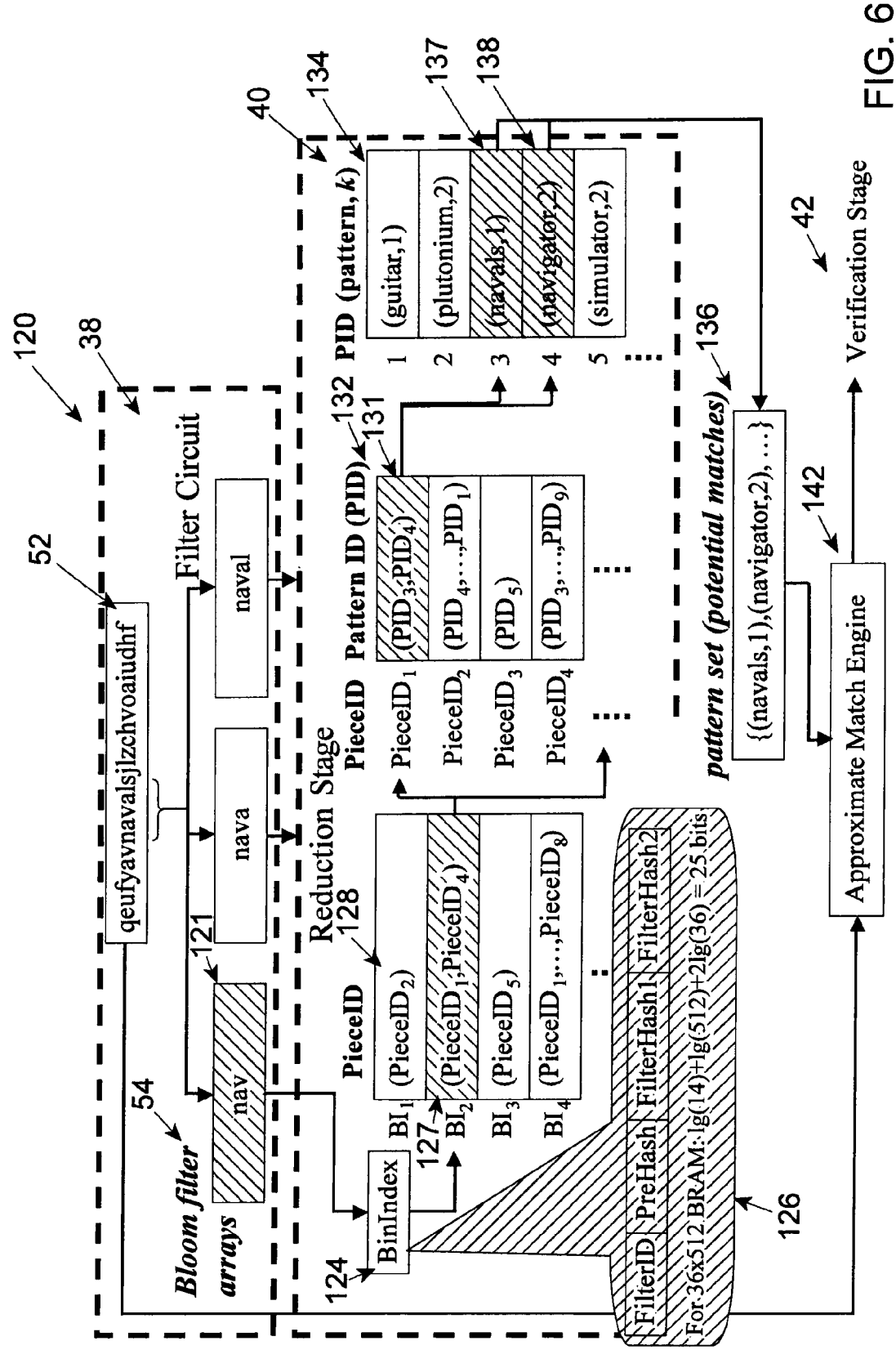
FIG. 6 provides an exemplary block diagram of a first reduction stage processing technique.

Utilizing the reduction stage 40 methodology shown in FIG. 6 with a series of index lookups, then given that at least one Bloom filter array 54 produces a match, the expected number of Bloom filter arrays 54 that will produce a match, i.e., the expected number of bin index lookups, is:

$$E[bins] \leq 1 + \frac{L}{\sigma^{\lfloor \frac{m}{k+1} \rfloor}} + Lf$$

Under the assumption that the pattern pieces are uniformly distributed over "L" Bloom filter arrays 54 (pattern piece lengths) and uniformly distributed over the bins, the expected number of pattern piece identifiers 128, as shown in FIG. 6, per bin is:

$$E[PieceIds/bin] \leq \frac{r(k+1)}{LW\left(\frac{B}{W}\right)^b}$$

where "B" is the size of memory used to implement the Bloom filter array 54, "W" is the number of words in the Bloom filter array 54 and "b" is the number of hash functions used in each Bloom filter in the Bloom filter array 54.

Finally, the expected number of patterns that specify a given pattern piece 131, as shown in FIG. 6, include:

$$E[patterns/PieceIDs] \leq 1 + \frac{r}{\sigma^{\lfloor \frac{m}{k+1} \rfloor}}$$

Therefore, provided that at least one Bloom filter array 54 produces a match, the expected pattern size is:

$$E[patterns] \leq \left(1 + \frac{L}{\sigma^{\lfloor m/k+1 \rfloor}} + Lf\right)\left(\frac{r(k+1)}{LW\left(\frac{B}{W}\right)^b}\right)\left(1 + \frac{r}{\sigma^{\lfloor \frac{m}{k+1} \rfloor}}\right)$$

Assuming uniform text, uniform distribution of piece lengths, uniform distributions (good hash functions) and with L=14, σ=40, r=14,000, b=3 and W=512, then the expected pattern set size is less than ten (10) for practical values of m and k (pattern length and allowable errors). The expected pattern set size quickly approaches one (1) as the alphabet size and/or pattern size increases.

The expression for the expected pattern set size when using other reduction stage approach indicated by FIG. 7 with the text segment as an index are similar and produce a slightly smaller pattern set size. In combination with the previous result, which is one pattern match every twelve (12) cycles, a conservative constraint for the average throughput of the verification stage 42 is approximately one (1) match on one pattern per every cycle.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

The invention claimed is:

1. A method for inspecting a data stream for data segments approximately matching any of a plurality of patterns, the method comprising:

filtering a plurality of data substrings within the data stream with a plurality of parallel filter mechanisms to thereby detect a plurality of potential matches between the data substrings and a plurality of pattern pieces, each pattern piece corresponding to at least one pattern, each data substring comprising a plurality of symbols;

reducing the detected potential matches to a plurality of pattern sets, each pattern set comprising (1) data representative of at least one pattern corresponding to a pattern piece which was a potential match to a data substring, and (2) data representative of an allowable error associated with the at least one pattern;

providing the pattern sets to a verification stage; and verifying with the verification stage whether a data segment within the data stream is an approximate match to a pattern within a provided pattern set on the basis of the allowable error data within that provided pattern set.

2. The method according to claim 1, further comprising, prior to the filtering step, receiving the data stream from a member of the group consisting of a communication link, a redundant array of independent disks ("RAID"), and a storage area network ("SAN").

3. The method according to claim 1, wherein the plurality of parallel filter mechanisms is a member of the group consisting of a set of parallel Bloom filters, a set of parallel Bloom filter arrays and a set of parallel Bloom filter arrays that utilize a single hash key generator.

4. The method according to claim 3, wherein the reducing step further includes performing the following steps with a reduction stage that is in communication with the plurality of parallel filter mechanisms:

utilizing data from the plurality of parallel filter mechanisms to lookup one or more pattern piece identifiers for at least one pattern piece that produced a potential match in the plurality of parallel filter mechanisms;

utilizing the one or more pattern piece identifiers for retrieving at least one pattern identifier; and utilizing the at least one retrieved pattern identifier for retrieving the data representative of at least one pattern and the data representative of the allowable error associated with the at least one pattern to thereby determine at least a portion of a pattern set.

5. The method according to claim 3, wherein the reducing step further includes performing the following steps with a reduction stage that is in communication with the plurality of parallel filter mechanisms:

utilizing each data sub string that produced a potential match for retrieving at least one pattern identifier; and utilizing the at least one retrieved pattern identifier for retrieving the data representative of at least one pattern and the data representative of the allowable error associated with the at least one pattern to thereby determine at least a portion of a pattern set.

6. The method according to claim 1, further comprising performing the reducing step with a reduction stage that is in communication with the plurality of parallel filter mechanisms, wherein the plurality of parallel filter mechanisms are implemented on a member of the group consisting of at least one reconfigurable logic device and at least one integrated circuit, and wherein the reduction stage is implemented on a member of the group consisting of at least one reconfigurable logic device and at least one integrated circuit.

7. The method according to claim 1, further comprising performing the reducing step with a reduction stage that is in communication with the plurality of parallel filter mechanisms, wherein the plurality of parallel filter mechanisms are implemented on a member of the group consisting of at least one Field Programmable Gate Array ("FPGA") and at least one Application-Specific Integrated Circuit ("ASIC"), and wherein the reduction stage is implemented on a member of the group consisting of at least one Field Programmable Gate Array ("FPGA") and at least one Application-Specific Integrated Circuit ("ASIC").

8. The method according to claim 1, wherein the plurality of parallel filter mechanisms include at least one Bloom filter array that is programmed with the pattern pieces, wherein the at least one Bloom filter array utilizes a single hash key generator for computing hash values that correspond to a bit vector and positions in the bit vector that identify whether a data substring is a potential match with one of the pattern pieces, the bit vector being stored in the Bloom filter array.

9. The method according to claim 1, wherein the reducing step further includes performing the following steps with a reduction stage that is in communication with the plurality of parallel filter mechanisms:

utilizing data from the plurality of parallel filter mechanisms to lookup one or more pattern piece identifiers for at least one pattern piece that produced a potential match in the plurality of parallel filter mechanisms;

utilizing the one or more pattern piece identifiers for retrieving at least one pattern identifier; and utilizing the at least one retrieved pattern identifier for retrieving the data representative of at least one pattern and the data representative of the allowable error associated with the at least one pattern to thereby determine at least a portion of a pattern set.

10. The method according to claim 9, wherein the reducing step further includes utilizing a first lookup function with a bin index.

11. The method according to claim 10, wherein the bin index is selected from the group consisting of different hash keys and portions of hash keys.

12. The method according to claim 1, wherein the reducing step further includes performing the following steps with a reduction stage that is in communication with the plurality of parallel filter mechanisms:

utilizing each data substring that produced a potential match for retrieving at least one pattern identifier; and utilizing the at least one retrieved pattern identifier for retrieving the data representative of at least one pattern and the data representative of the allowable error associated with the at least one pattern to thereby determine at least a portion of a pattern set.

13. A system for inspecting a data stream for data segments approximately matching any of a plurality of patterns, the system comprising:
- a plurality of parallel filter mechanisms each configured to filter a plurality of data substrings within the data stream to thereby detect a plurality of potential matches between the data substrings and a plurality of pattern pieces, each pattern piece corresponding to at least one pattern, each data substring comprising a plurality of symbols;
- a reduction stage configured to reduce the detected potential matches to a plurality of pattern sets, each pattern set comprising (1) data representative of at least one pattern corresponding to a pattern piece which was a potential match to a data substring, and (2) data representative of an allowable error associated with the at least one pattern; and
- a verification stage configured to receive the pattern sets and verify whether a data segment within the data stream is an approximate match to a pattern within a received pattern set on the basis of the allowable error data within that received pattern set.

14. The system according to claim 13, further comprising a data stream provider selected as at least one member from the group consisting of a communication link, a redundant array of independent disks ("RAID"), and a storage area network ("SAN").

15. The system according to claim 13, wherein the plurality of parallel filter mechanisms is a member of the group consisting of a set of parallel Bloom filters, a set of parallel Bloom filter arrays and a set of parallel Bloom filter arrays that utilize a single hash key generator.

16. The system according to claim 15, wherein the reduction stage is further configured to:
- look up, on the basis of data from the plurality of parallel filter mechanisms, one or more pattern piece identifiers for at least one pattern piece that produced a potential match in the plurality of parallel filter mechanisms;
- retrieve, on the basis of the one or more looked up pattern piece identifiers, at least one pattern identifier; and
- retrieve, on the basis of the at least one retrieved pattern identifier, the data representative of at least one pattern and the data representative of the allowable error associated with the at least one pattern to thereby determine at least a portion of a pattern set.

17. The system according to claim 15, wherein the reduction stage is further configured to:
- retrieve, on the basis of each data substring that produced a potential match, at least one pattern identifier; and
- retrieve, on the basis of the at least one retrieved pattern identifier, the data representative of at least one pattern and the data representative of the allowable error associated with the at least one pattern to thereby determine at least a portion of a pattern set.

18. The system according to claim 13, wherein the plurality of parallel filter mechanisms are implemented on a member of the group consisting of at least one reconfigurable logic device and at least one integrated circuit, and wherein the reduction stage is implemented on a member of the group consisting of at least one reconfigurable logic device and at least one integrated circuit.

19. The system according to claim 13, wherein the plurality of parallel filter mechanisms are implemented on a member of the group consisting of at least one Field Programmable Gate Array ("FPGA") and at least one Application-Specific Integrated Circuit ("ASIC"), and wherein the reduction stage is implemented on a member of the group consisting of at least one Field Programmable Gate Array ("FPGA") and at least one Application-Specific Integrated Circuit ("ASIC").

20. The system according to claim 13, wherein the plurality of parallel filter mechanisms includes at least one Bloom filter array that is programmed with the pattern pieces, wherein the at least one Bloom filter array is configured to utilize a single hash key generator for computing hash values that correspond to (1) a position of a particular Bloom filter in the at least one Bloom filter array and (2) a bit vector stored by the particular Bloom filter, and (3) positions of bits in the bit vector that identify whether a data substring is a potential match with at least one of the pattern pieces.

21. The system according to claim 13, wherein the reduction stage is further configured to:
- look up, on the basis of data from the plurality of parallel filter mechanisms, one or more pattern piece identifiers for at least one pattern piece that produced a potential match in the plurality of parallel filter mechanisms;
- retrieve, on the basis of the one or more looked up pattern piece identifiers, at least one pattern identifier; and
- retrieve, on the basis of the at least one retrieved pattern identifier, the data representative of at least one pattern and the data representative of the allowable error associated with the at least one pattern to thereby determine at least a portion of a pattern set.

22. The system according to claim 21, wherein the reduction stage is further configured to utilize a first lockup function with a bin index.

23. The system according to claim 22, wherein the bin index is selected as a member from the group consisting of different hash keys and portions of hash keys.

24. The system according to claim 13, wherein the reduction stage is further configured to:
- retrieve, on the basis of each data substring that produced a potential match, at least one pattern identifier; and
- retrieve, on the basis of the at least one retrieved pattern identifier, the data representative of at least one pattern and the data representative of the allowable error associated with the at least one pattern to thereby determine at least a portion of a pattern set.

25. A method for processing a plurality of data substrings within a data string for facilitating a determination as to whether the data string contains an approximate match to any of a plurality of patterns, the data string comprising a plurality of data symbols, the method comprising:
- querying a filter circuit with the data sub strings to detect a plurality of potential matches, each potential match representing a potential match between a data substring and a pattern piece, wherein each pattern of a plurality of the patterns comprises a plurality of corresponding pattern pieces, the filter circuit being programmed with the pattern pieces;
- applying the detected potential matches to a reduction stage to determine a plurality of pattern sets, each pattern set corresponding to a detected potential match and comprising (1) data representative of a pattern which corresponds to the pattern piece which produced the corresponding potential match, and (2) data representative of an allowable error associated with that pattern; and
- delivering the determined pattern sets to an approximate match engine for a determination as to whether at least a portion of the data string is an approximate match to any of the patterns within the delivered pattern sets taking into consideration the allowable error data within the delivered pattern sets.

26. The method according to claim 25 wherein the filter circuit comprises a Bloom filter circuit.

27. The method according to claim 26 further comprising:
determining with the approximate match engine whether any approximate matches exist between the data string portion and the patterns within the delivered pattern sets taking into consideration the allowable error data within the delivered pattern sets.

28. The method according to claim 27 further comprising:
slicing the patterns of at least a plurality of the patterns into a plurality of the pattern pieces; and
programming the Bloom filter circuit with the pattern pieces.

29. The method according to claim 27 further comprising:
performing the querying step and the applying step in a pipelined manner.

30. The method according to claim 29 further comprising:
performing the querying step and the applying step with reconfigurable hardware.

31. The method according to claim 30 further comprising:
performing the determining step with reconfigurable hardware.

32. The method according to claim 29 further comprising:
performing the querying step and the applying step with at least one integrated circuit.

33. The method according to claim 29 wherein the pattern pieces comprise a plurality of pattern pieces of different lengths.

34. The method according to claim 33 wherein the pattern pieces corresponding to the same pattern are non-overlapping with each other.

35. The method according to claim 34 wherein the Bloom filter circuit comprises a plurality of parallel Bloom filter circuits, each of the parallel Bloom filter circuits being programmed with pattern pieces of the same length such that each parallel Bloom filter circuit corresponds to a different pattern piece length than the other parallel Bloom filter circuits, and wherein the querying step comprises simultaneously providing the parallel Bloom filter circuits with a plurality of the data substrings in parallel.

36. The method according to claim 35 wherein the Bloom filter circuit further comprises a shift register for storing at least a portion of the data string, the method further comprising:
streaming the data symbols of the data string through the shift register; and
reading the data substrings for the querying step out of the shift register.

37. The method according to claim 36 wherein the streaming step comprises streaming a plurality of new symbols of the data string into the shift register per cycle, and wherein the reading step comprises reading a plurality of different substrings for the querying step out of the shift register per cycle.

38. The method according to claim 35 wherein each parallel Bloom filter circuit is configured to store a plurality of bit vectors, each bit vector comprising a plurality of bits, each bit having a value, and wherein the querying step further comprises:
applying each data substring to at least one hash function to generate at least one hash key;
retrieving a bit vector from a parallel Bloom filter circuit based on the at least one generated hash key;
selecting a plurality of bit positions in the retrieved bit vector based on the at least one generated hash key; and
determining whether a potential match exists between that data substring and a pattern piece based on the values of the bits at the selected bit positions.

39. The method according to claim 38 wherein the step of applying each data substring to at least one hash function comprises applying each data substring to a plurality of hash functions to generate a plurality of hash keys, wherein the bit vector retrieving step comprises retrieving a bit vector from a parallel Bloom filter circuit based on a generated hash key, and wherein the bit position selecting step comprises selecting a plurality of bit positions in the retrieved bit vector based on a plurality of the other generated hash keys.

40. The method according to claim 38 wherein the step of applying each data substring to at least one hash function comprises applying each data substring to a single hash function to generate a single hash key, wherein the bit vector retrieving step comprises retrieving a bit vector from a parallel Bloom filter circuit based on a portion of the generated hash key, and wherein the bit position selecting step comprises selecting a plurality of bit positions in the retrieved bit vector based on another portion of the generated hash key.

41. The method according to claim 38 wherein the reduction stage is configured to (1) store a plurality of pattern piece identifiers, each pattern piece identifier being indexed by data produced as a result of the querying step, (2) store a plurality of pattern identifiers, each pattern identifier being indexed by a pattern piece identifier, and (3) store a plurality of pattern set pairs, each pattern set pair being indexed by a pattern identifier, each pattern set pair comprising (a) data representative of a pattern, and (b) data representative of an allowable error associated with that pattern, and wherein the potential match applying step comprises:
retrieving at least one of the stored pattern piece identifiers based on data produced as a result of the querying step;
retrieving at least one of the stored pattern identifiers based on each retrieved pattern piece identifier; and
retrieving at least one of the stored pattern set pairs based on each retrieved pattern identifier, the retrieved at least one pattern set pair defining at least a portion of a pattern set.

42. The method according to claim 41 wherein the pattern piece identifier retrieving step comprises retrieving at least one of the stored pattern piece identifiers based on data corresponding to the at least one generated hash key.

43. The method according to claim 38 wherein the reduction stage is configured to (1) store a plurality of pattern identifiers, each pattern identifier being indexed by a pattern piece, and (2) store a plurality of pattern set pairs, each pattern set pair being indexed by a pattern identifier, each pattern set pair comprising (a) data representative of a pattern, and (b) data representative of an allowable error associated with that pattern, and wherein the potential match applying step comprises:
retrieving at least one of the stored pattern identifiers based on the data substring that produced a potential match; and
retrieving at least one of the stored pattern set pairs based on each retrieved pattern identifier, the retrieved at least one pattern set pair defining at least a portion of a pattern set.

44. The method according to claim 43 wherein the reduction stage comprises a plurality of data structures for storing the pattern identifiers, each data structure corresponding to pattern pieces of the same length such that each data structure also corresponds to a different pattern piece length than the other data structures.

45. The method according to claim 44 wherein the data structures comprise a plurality of hash tables.

46. The method according to claim 44 wherein the data structures comprise a plurality of balanced search trees.

47. The method according to claim 29 wherein the applying step comprises eliminating any potential matches that are false positives.

48. The method according to claim 27 wherein the data representative of an allowable error comprises a predetermined number of allowable errors.

49. The method according to claim 25 wherein the reduction stage is configured to (1) store a plurality of pattern piece identifiers, each pattern piece identifier being indexed by data produced as a result of the querying step, (2) store a plurality of pattern identifiers, each pattern identifier being indexed by a pattern piece identifier, and (3) store a plurality of pattern set pairs, each pattern set pair being indexed by a pattern identifier, each pattern set pair comprising (a) data representative of a pattern, and (b) data representative of an allowable error associated with that pattern, and wherein the potential match applying step comprises:

retrieving at least one of the stored pattern piece identifiers based on data produced as a result of the querying step;

retrieving at least one of the stored pattern identifiers based on each retrieved pattern piece identifier, and retrieving at least one of the stored pattern set pairs based on each retrieved pattern identifier, the retrieved at least one pattern set pair defining at least a portion of a pattern set.

50. The method according to claim 49 wherein the querying step comprises applying each data substring to at least one hash function to generate at least one hash key, and wherein the pattern piece identifier retrieving step comprises retrieving at least one of the stored pattern piece identifiers based on data corresponding to the at least one generated hash key.

51. The method according to claim 25 wherein the reduction stage is configured to (1) store a plurality of pattern identifiers, each pattern identifier being indexed by a pattern piece, and (2) store a plurality of pattern set pairs, each pattern set pair being indexed by a pattern identifier, each pattern set pair comprising (a) data representative of a pattern, and (b) data representative of an allowable error associated with that pattern, and wherein the potential match applying step comprises:

retrieving at least one of the stored pattern identifiers based on the data substring that produced a potential match; and retrieving at least one of the stored pattern set pairs based on each retrieved pattern identifier, the retrieved at least one pattern set pair defining at least a portion of a pattern set.

52. The method according to claim 51 wherein the reduction stage comprises a plurality of data structures for storing the pattern identifiers, each data structure corresponding to pattern pieces of the same length such that each data structure also corresponds to a different pattern piece length than the other data structures.

53. The method according to claim 52 wherein the data structures comprise a plurality of hash tables.

54. The method according to claim 52 wherein the data structures comprise a plurality of balanced search trees.

55. The method according to claim 25 wherein the patterns and the data string are representative of text.

56. The method according to claim 25 wherein the allowable error data comprises an edit distance value.

57. A system for processing a plurality of data substrings within a data string for facilitating a determination as to whether the data string contains an approximate match to any of a plurality of patterns, the data string comprising a plurality of data symbols, the system comprising:

a filter circuit configured to be queried by the data substrings to detect a plurality of potential matches, each potential match representing a potential match between a data substring and a pattern piece, wherein each pattern of a plurality of the patterns comprises a plurality of corresponding pattern pieces, the filter circuit being programmed with the pattern pieces; and a reduction stage in communication with the filter circuit, the reduction stage being configured to (1) process the detected potential matches, (2) determine a plurality of pattern sets in response to the processing, each pattern set corresponding to a potential match and comprising (a) data representative of a pattern which corresponds to the pattern piece which produced the corresponding potential match, and (b) data representative of an allowable error associated with that pattern, and (3) output the determined pattern sets for communication to an approximate match engine for a determination as to whether at least a portion of the data string is an approximate match to any of the patterns within the determined pattern sets taking into consideration the allowable error data within the determined pattern sets.

58. The system according to claim 57 wherein the filter circuit comprises a Bloom filter circuit.

59. The system according to claim 58 further comprising:

an approximate match engine in communication with the reduction stage, the approximate match engine configured to determine whether any approximate matches exist between the data string portion and the patterns within the determined pattern sets taking into consideration the allowable error data within the determined pattern sets.

60. The system according to claim 59 wherein the Bloom filter circuit and the reduction stage are configured to operate in a pipelined manner.

61. The system according to claim 60 wherein the Bloom filter circuit and the reduction stage are implemented with as hardware circuitry.

62. The system according to claim 61 wherein the approximate match engine is implemented with hardware circuitry.

63. The system according to claim 61 wherein the hardware circuitry comprises reconfigurable hardware.

64. The system according to claim 61 wherein the hardware circuitry comprises at least one integrated circuit.

65. The system according to claim 64 wherein the at least one integrated circuit comprises at least one Application Specific Integrated Circuit ("ASIC").

66. The system according to claim 60 wherein the pattern pieces comprise a plurality of pattern pieces of different lengths.

67. The system according to claim 66 wherein the pattern pieces corresponding to the same pattern are non-overlapping with each other.

68. The system according to claim 67 wherein the Bloom filter circuit comprises a plurality of parallel Bloom filter circuits, each of the parallel Bloom filter circuits being programmed with pattern pieces of the same length such that each parallel Bloom filter circuit corresponds to a different pattern piece length than the other parallel Bloom filter circuits, and wherein the Bloom filter circuit is further configured to simultaneously provide the parallel Bloom filter circuits with a plurality of the data sub strings in parallel.

69. The system according to claim 68 wherein the Bloom filter circuit further comprises a shift register for storing at least a portion of the data string, and wherein the Bloom filter circuit is further configured to (1) stream the data symbols of the data string through the shift register and (2) read the data substrings out of the shift register for delivery to the parallel Bloom filter circuits.

70. The system according to claim 69 wherein the Bloom filter circuit is further configured to (1) stream a plurality of new symbols of the data string into the shift register per cycle, and (2) read a plurality of different substrings out of the shift register per cycle for delivery to the parallel Bloom filter circuits.

71. The system according to claim 68 wherein each parallel Bloom filter circuit is configured to store a plurality of bit vectors, each bit vector comprising a plurality of bits, each bit having a value, and wherein the Bloom filter circuit is further configured to (1) apply each data sub string to at least one hash function to generate at least one hash key, (2) retrieve a bit vector from a parallel Bloom filter circuit based on the at least one generated hash key, (3) select a plurality of bit positions in the retrieved bit vector based on the at least one generated hash key, and (4) determine whether a potential match exists between that data substring and a pattern piece based on the values of the bits at the selected bit positions.

72. The system according to claim 71 wherein each parallel Bloom filter circuit is further configured to (1) apply each data sub string to a plurality of hash functions to generate a plurality of hash keys, (2) retrieve a bit vector from a parallel Bloom filter circuit based on a generated hash key, and (3) select a plurality of bit positions in the retrieved bit vector based on a plurality of the other generated hash keys.

73. The system according to claim 71 wherein each parallel Bloom filter circuit is further configured to (1) apply each data sub string to a single hash function to generate a single hash key, (2) retrieve a bit vector from a parallel Bloom filter circuit based on a portion of the generated hash key, and (3) select a plurality of bit positions in the retrieved bit vector based on another portion of the generated hash key.

74. The system according to claim 71 wherein the reduction stage comprises a first table, a second table, and a third table, wherein the first table is configured to store a plurality of pattern piece identifiers, each pattern piece identifier being indexed by data produced by the Bloom filter circuit, wherein the second table is configured to store a plurality of pattern identifiers, each pattern identifier being indexed by a pattern piece identifier, and wherein the third table is further configured to store a plurality of pattern set pairs, each pattern set pair being indexed by a pattern identifier, each pattern set pair comprising (a) data representative of a pattern, and (b) data representative of an allowable error associated with that pattern, and wherein the reduction stage is further configured to (1) retrieve at least one of the stored pattern piece identifiers from the first table based on data produced by the Bloom filter circuit, (2) retrieve at least one of the stored pattern identifiers from the second table based on each retrieved pattern piece identifier, and (3) retrieve at least one of the stored pattern set pairs from the third table based on each retrieved pattern identifier, the at least one retrieved pattern set pair defining at least a portion of a pattern set.

75. The system according to claim 74 wherein the reduction stage is further configured to retrieve at least one of the stored pattern piece identifiers from the first table based on data corresponding to the at least one generated hash key.

76. The system according to claim 71 wherein the reduction stage comprises a first data structure and a second data structure, wherein the first data structure is configured to store a plurality of pattern identifiers, each pattern identifier being indexed by a pattern piece, and wherein the second data structure is configured to store a plurality of pattern set pairs, each pattern set pair being indexed by a pattern identifier, each pattern set pair comprising (a) data representative of a pattern, and (b) data representative of an allowable error associated with that pattern, and wherein the reduction stage is further configured to (1) retrieve at least one of the stored pattern identifiers from the first data structure based on the data substring that produced a potential match, and (2) retrieve at least one of the stored pattern set pairs from the second data structure based on each retrieved pattern identifier, the at least one retrieved pattern set pair defining at least a portion of a pattern set.

77. The system according to claim 76 wherein the first data structure comprises a plurality of the first data structures, each first data structure corresponding to pattern pieces of a different length such that each first data structure also corresponds to a different pattern piece length than the other first data structures.

78. The system according to claim 77 wherein the first and second data structures comprise a plurality of hash tables.

79. The system according to claim 77 wherein the first and second data structures comprise a plurality of balanced search trees.

80. The system according to claim 60 wherein the reduction stage is further configured to eliminate any potential matches that are false positives.

81. The system according to claim 59 wherein the data representative of an allowable error comprises a predetermined number of allowable errors.

82. The system according to claim 57 wherein the reduction stage comprises a first table, a second table, and a third table, wherein the first table is configured to store a plurality of pattern piece identifiers, each pattern piece identifier being indexed by data produced by the filter circuit, wherein the second table is configured to store a plurality of pattern identifiers, each pattern identifier being indexed by a pattern piece identifier, and wherein the third table is further configured to store a plurality of pattern set pairs, each pattern set pair being indexed by a pattern identifier, each pattern set pair comprising (a) data representative of a pattern, and (b) data representative of an allowable error associated with that pattern, and wherein the reduction stage is further configured to (1) retrieve at least one of the stored pattern piece identifiers from the first table based on data produced by the Bloom filter circuit, (2) retrieve at least one of the stored pattern identifiers from the second table based on each retrieved pattern piece identifier, and (3) retrieve at least one of the stored pattern set pairs from the third table based on each retrieved pattern identifier, the at least one retrieved pattern set pair defining at least a portion of a pattern set.

83. The system according to claim 82 wherein the filter circuit is further configured to apply each data substring to at least one hash function to generate at least one hash key, and wherein the reduction stage is further configured to retrieve at least one of the stored pattern piece identifiers from the first table based on data corresponding to the at least one generated hash key.

84. The system according to claim 58 wherein the reduction stage comprises a first data structure and a second data structure, wherein the first data structure is configured to store a plurality of pattern identifiers, each pattern identifier being indexed by a pattern piece, and wherein the second data structure is configured to store a plurality of pattern set pairs, each pattern set pair being indexed by a pattern identifier, each pattern set pair comprising (a) data representative of a pattern, and (b) data representative of an allowable error associated with that pattern, and wherein the reduction stage is further configured to (1) retrieve at least one of the stored pattern identifiers from the first data structure based on the data substring that produced a potential match, and (2) retrieve at least one of the stored pattern set pairs from the second data structure based on each retrieved pattern identifier, the at least one retrieved pattern set pair defining at least a portion of a pattern set.

85. The system according to claim 84 wherein the first data structure comprises a plurality of the first data structures, each first data structure corresponding to pattern pieces of a different length such that each first data structure also corresponds to a different pattern piece length than the other first data structures.

86. The system according to claim 85 wherein the first and second data structures comprise a plurality of hash tables.

87. The system according to claim 85 wherein the first and second data structures comprise a plurality of balanced search trees.

88. The system according to claim 57 wherein the patterns and the data string are representative of text.

89. A method comprising:
electronically processing a sub string of an input string with a filter circuit to find a possible match between the input substring and a substring of a query string, electronically determining an allowable error value with a reduction circuit based at least in part on the possible match; and
electronically delivering the input string and the determined allowable error value to a verification circuit for a determination as to whether the input string is an approximate match to the query string based at least in part on the determined allowable error value.

90. The method according to claim 89 further comprising:
electronically performing an approximate match operation with the verification circuit to determine whether the input string is an approximate match to the query string based at least in part on the determined allowable error value.

91. The method according to claim 89 wherein the filter circuit comprises a reconfigurable hardware circuit.

92. The method according to claim 89 wherein the reduction circuit comprises a reconfigurable hardware circuit.

93. An approximate matching apparatus comprising:
a circuit configured to (1) process a substring of an input string to find a possible match between the input substring and a substring of a query string, (2) determine an allowable error value based at least in part on the possible match, and (3) perform an approximate match operation to determine whether the input string is an approximate match to the query string based at least in part on the determined allowable error value.

94. The apparatus according to claim 93 wherein the circuit comprises a reconfigurable hardware circuit.

95. The apparatus according to claim 93 wherein the circuit comprises a filter circuit, a reduction circuit, and a verification circuit, the filter circuit configured to process a substring of an input string to find a possible match between the input substring and a sub string of a query string, the reduction circuit configured to determine an allowable error value based at least in part on the possible match, and the verification circuit configured to perform an approximate match operation to determine whether the input string is an approximate match to the query string based at least in part on the determined allowable error value.

* * * * *